US012115393B2

(12) United States Patent
Bouakaz et al.

(10) Patent No.: US 12,115,393 B2
(45) Date of Patent: Oct. 15, 2024

(54) METHODS FOR SETTING PARAMETERS OF A NEUROSTIMULATION DEVICE AND ASSOCIATED DEVICES

(71) Applicants: INSTITUT NATIONAL DE LA SANTE ET DE LA RECHERCHE MEDICALE (INSERM), Paris (FR); UNIVERSITÉ DE TOURS, Tours (FR)

(72) Inventors: Ayache Bouakaz, Tours (FR); Catherine Belzung, Tours (FR)

(73) Assignees: INSTITUT NATIONAL DE LA SANTE ET DE LA RECHERCHE MEDICALE (INSERM), Paris (FR); UNIVERSITÉ DE TOURS, Tours (FR)

( * ) Notice: Subject to any disclaimer, the term of this patent is extended or adjusted under 35 U.S.C. 154(b) by 270 days.

(21) Appl. No.: 17/609,542

(22) PCT Filed: May 11, 2020

(86) PCT No.: PCT/IB2020/054436
§ 371 (c)(1),
(2) Date: Nov. 8, 2021

(87) PCT Pub. No.: WO2020/230003
PCT Pub. Date: Nov. 19, 2020

(65) Prior Publication Data
US 2022/0226671 A1    Jul. 21, 2022

(30) Foreign Application Priority Data

May 10, 2019    (WO) .................. PCT/IB2019/000568

(51) Int. Cl.
*A61N 7/00*         (2006.01)
*G16H 20/30*        (2018.01)

(52) U.S. Cl.
CPC .............. *A61N 7/00* (2013.01); *G16H 20/30* (2018.01); *A61N 2007/0026* (2013.01); *A61N 2007/0073* (2013.01); *A61N 2007/0078* (2013.01)

(58) Field of Classification Search
CPC .............. A61N 2007/0026; A61N 7/00; A61N 2007/0004; A61N 2007/0021; A61N 2007/003
See application file for complete search history.

(56) References Cited

U.S. PATENT DOCUMENTS

2003/0204135 A1    10/2003  Bystritsky
2012/0089205 A1*    4/2012  Boyden ................ A61N 5/0601
                                                      607/88

(Continued)

OTHER PUBLICATIONS

Hyungmin et al: "Focused Ultrasound-mediated Non-invasive Brain Stimulation: Examination of Sonication Parameters", Brain Stimulation, vol. 7, No. 5, p. 748-756, Jul. 2, 2014.

(Continued)

*Primary Examiner* — Amelie R Davis
(74) *Attorney, Agent, or Firm* — WC&F IP

(57) ABSTRACT

The present invention relates the field of ultrasound and neurostimulation. The inventors have shown that using ultrasound neurostimulation with specific parameters provides similar or better effects that fluoxetine administration in depression. Such assessment was made in unpredictable chronic mild stress model in mouse. The proposed use also provides with positive effects in other cases, such as modulating emotion or attenuating anxiety-related behaviours (stress notably).

20 Claims, 12 Drawing Sheets

(56) References Cited

U.S. PATENT DOCUMENTS

| | | |
|---|---|---|
| 2016/0001096 A1 | 1/2016 | Mishelevich |
| 2017/0080255 A1* | 3/2017 | Law ................... G10K 11/346 |
| 2018/0214691 A1* | 8/2018 | Famm ................ A61N 1/36139 |
| 2019/0038922 A1* | 2/2019 | Carpentier ............. A61B 8/481 |
| 2020/0016435 A1* | 1/2020 | Bowers ................... A61N 7/00 |

OTHER PUBLICATIONS

King et al: "Effective Parameters for Ultrasound-Induced In Vivo Neurostimulation", Ultrasound in Medicine and Biology, vol. 39, No. 2, p. 312-331, Feb. 1, 2013.

* cited by examiner

METHODS FOR SETTING PARAMETERS OF A NEUROSTIMULATION DEVICE AND ASSOCIATED DEVICES

TECHNICAL FIELD OF THE INVENTION

The present invention concerns a method for setting parameters of a neurostimulation device before stimulating cerebral activity of a subject. Such method can be used in a method for modulating emotion. The present invention also relates to an associated controller, an associated neurostimulation device, an associated computer program product and an associated computer-readable medium.

BACKGROUND OF THE INVENTION

Ultrasound has been used for many medical applications, and is generally known as cyclic sound pressure with a frequency greater than the upper limit of human hearing. The production of ultrasound is used in many different fields, typically to penetrate a medium and measure the reflection signature or to supply focused energy. For example, the reflection signature can reveal details about the inner structure of the medium. A well-known application of this technique is its use in sonography to produce a picture of a fetus in a womb. There are other applications which may provide therapeutic effects, such as lithotripsy for ablation of kidney stones or high-intensity focused ultrasound for thermal ablation of brain tumors.

A benefit of ultrasound therapy is its non-invasive nature. Neuromodulation techniques such as deep brain stimulation and repetitive transcranial magnetic stimulation have gained attention due to their therapeutic utility in the management of numerous neurological/psychiatric diseases. These methods for stimulating neuronal circuits have been demonstrated to hold promise for the treatment of such diseases and disorders as Parkinson's, Alzheimer's, coma, epilepsy, stroke, depression, schizophrenia, addiction, neurogenic pain, cognitive/memory dysfunction, and others.

Among these mentioned disorders and/or illnesses, major depression is one of the main factors contributing to the Global Burden of Disease. Current treatment strategies (e.g., antidepressants and neurostimulation techniques) of major depression show some limitations including inefficacy and invasiveness.

SUMMARY OF THE INVENTION

The invention aims at providing with a method and/or a device enabling to provide ultrasound therapy to neural tissue with at least a same level of accuracy than antidepressants.

To this end, the specification describes a method for setting parameters of a neurostimulation device before stimulating cerebral activity of a subject, the neurostimulation device comprising at least an ultrasound probe adapted to emit ultrasound pulses with a controllable ultrasound power, the neurostimulation device being adapted to stimulate cerebral activity by applying ultrasound pulses emitted by the at least one ultrasound probe, the method being computer-implemented and comprising the steps of providing a motor threshold excitation, the motor threshold excitation corresponding to the ultrasound power leading to 50% success of obtaining a motor response of the subject when stimulating the cerebral activity of the subject with the neurostimulation device, and tuning at least one parameter of the neurostimulation device based on the provided motor threshold excitation, the step of tuning comprising setting the ultrasound power of the pulses so that the ratio between the ultrasound power of the pulses and the motor threshold excitation be superior or equal to 1.2.

Thanks to such method, the neurostimulation device is adapted to produce an appropriate transcranial ultrasound neurostimulation.

In particular, the ultrasound neurostimulation obtained enabling to provide ultrasound therapy to neural tissue with at least a same level of efficacy than antidepressants.

Indeed, the inventors have shown that transcranial ultrasound neurostimulation (ultrasound neurostimulation) of the prefrontal cortex produced antidepressant-like effects and decreased anxiety related behaviors in a mouse model of major depression, microPET imaging enhanced by FDG and brain metabolomic analyses revealed that ultrasound neurostimulation triggered the activation of ultrasound targeted brain region in addition to brain areas at a distance from the targeted zone producing an anti-depressant-like effect.

This shows that well-controlled transcranial ultrasound neurostimulation has great potential for the treatment of major depression.

According to further aspects of this method for setting which are advantageous but not compulsory, the method for setting parameters might incorporate one or several of the following features, taken in any technically admissible combination:
- setting the ultrasound power of the pulses is implemented so that the ratio between the ultrasound power of the pulses and the motor threshold excitation is inferior to or equal to 2.0.
- setting the ultrasound power of the pulses is implemented so that the ratio between the ultrasound power of the pulses and the motor threshold excitation be comprised between 1.4 and 1.8.
- setting the ultrasound power of the pulses is implemented so that the ratio between the ultrasound power of the pulses and the motor threshold excitation be comprised between 1.55 and 1.65.
- the step of tuning further comprises setting the frequency of the pulses between 400 kilohertz and 600 kilohertz, preferably between 450 kilohertz and 550 kilohertz, more preferably between 490 kilohertz and 510 kilohertz.
- the step of tuning further comprises setting the number of cycles between 75000 and 80000, preferably between 78000 and 82000 and more preferably between 79000 and 81000, the number of cycles being the number of pulses applied during one application, an application being a set of uninterrupted ultrasound pulses.
- the step of tuning further comprises setting the number of ultrasound applications in one day, one application being a set of uninterrupted ultrasound pulses, the number of applications being set to a value comprised between 40 and 60, preferably between 45 and 55, more preferably between 48 and 52.
- the subject is a mammal, notably a rodent such as a mouse.
- the at least one parameter is set to enable the stimulation of the cerebral activity of the subject to treat a neuropathological illness and/or disorder.
- the neuropathological illness is depression.
- the at least one parameter is set to enable the stimulation of the cerebral activity of the subject to reduce anxiety-like behavior of the subject, notably stress of the subject.

the step of tuning further comprises setting the position of the ultrasound probe, the position of the ultrasound probe being set so that the ultrasound pulses be applied in the infralimbic cortex of the subject.

The specification also describes a method for modulating emotion, the method for modulating emotion comprising the steps of carrying out a method for setting parameters as previously described, and applying the ultrasound pulses with the neurostimulation device having parameters set in accordance with the method for setting parameters.

The specification also relates to a controller adapted to set parameters of a neurostimulation device before stimulating cerebral activity of a subject, the neurostimulation device comprising at least an ultrasound probe adapted to emit ultrasound pulses with a controllable ultrasound power, the neurostimulation device being adapted to stimulate cerebral activity by applying ultrasound pulses emitted by the at least one ultrasound probe, the controller being adapted to receive the motor threshold excitation, the motor threshold excitation corresponding to the ultrasound power leading to 50% success of obtaining a motor response of the subject when stimulating the cerebral activity of the subject with the neurostimulation device, and further adapted to tune at least one parameter of the neurostimulation device based on the provided motor threshold excitation, the step of tuning comprising setting the ultrasound power of the pulses so that the ratio between the ultrasound power of the pulses and the motor threshold excitation be superior or equal to 1.2.

The specification describes a neurostimulation device comprising at least an ultrasound probe adapted to emit ultrasound pulses with a controllable ultrasound power and a controller as previously described. The neurostimulation device is adapted to stimulate cerebral activity by applying ultrasound pulses emitted by the at least one ultrasound probe.

The specification also relates to a computer program product comprising computer program instructions, the computer program instructions being loadable into a data-processing unit and adapted to cause execution at least one step of the method as previously described when run by the data-processing unit.

The specification describes a computer-readable medium comprising computer program instructions which, when executed by a data-processing unit, cause execution at least one step of the method as previously described.

The specification also deals with a method for treating neuropathological illnesses and/or disorders. The method for treating neuropathological illnesses and/or disorders comprises the steps of carrying out a method for setting parameters as previously described, and applying the ultrasound pulses with the neurostimulation device having parameters set in accordance with the method for setting parameters.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Description of the System

General Description of the Neurostimulation Device

Figure 1:
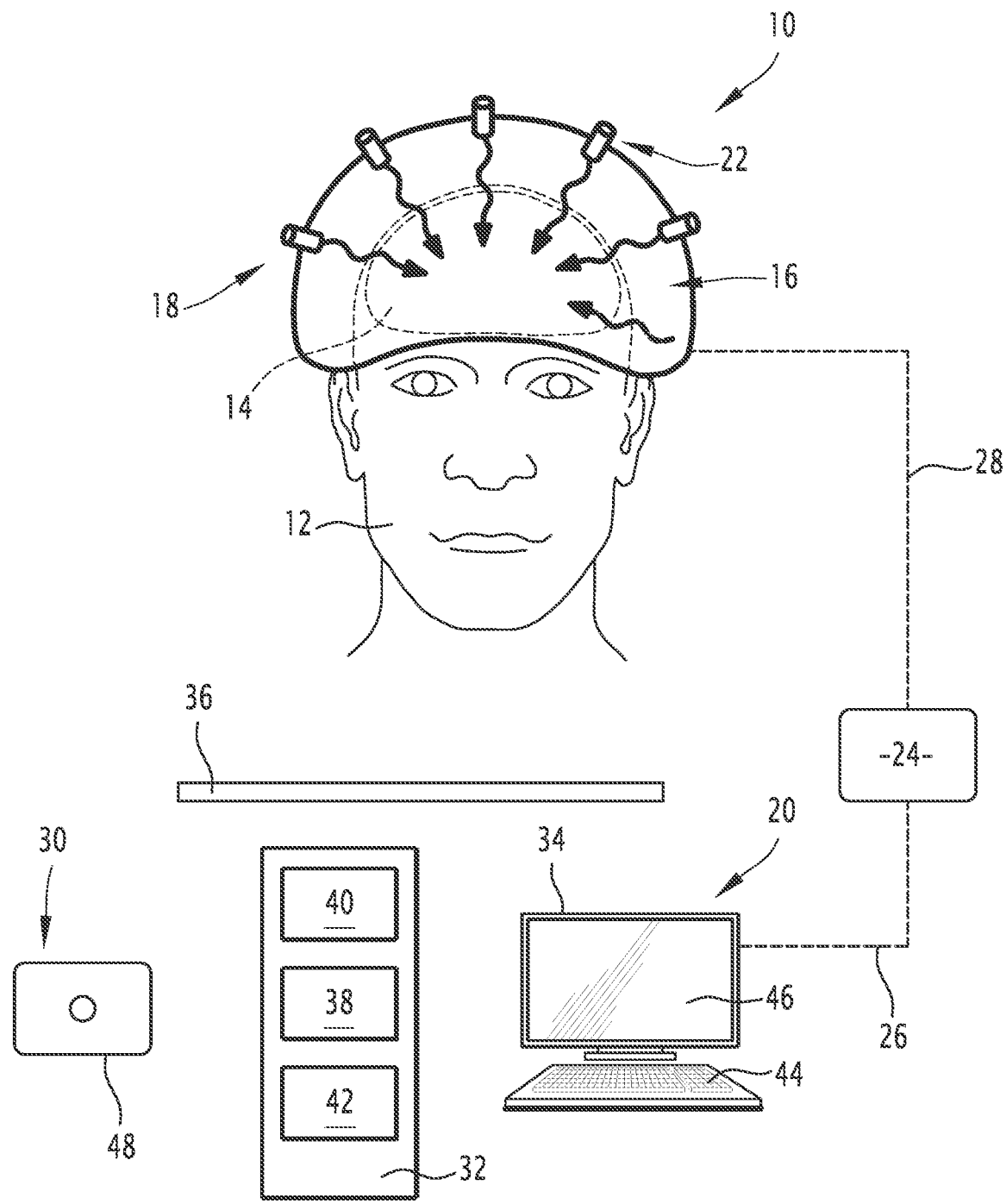
FIG. 1 shows schematically a neurostimulation device.

A neurostimulation device 10 is represented schematically in FIG. 1.

The neurostimulation device 10 is adapted to stimulate cerebral activity of a subject 12.

The subject 12 which is represented in FIG. 1 is a human for which the face and the brain 14 are shown.

More generally, the subject 12 is a living subject and notably an animal.

As a specific example, the subject 12 is a mammal.

In the experimental section, the results are provided for a rodent, and a mouse in particular.

The neurostimulation device 10 comprises a body 16, one ultrasound probe 18 and a controller 20.

Description of the Body 16

In the example, the body 16 is a helmet.

More generally, the body 16 is a headgear such as a cap, a headband, a helmet, a protective head covering, a hood, a stretchable material, a flexible material similar to a scarf that can be tied on the head, or other headgear that may be adapted to hold components for generating sound waves and/or other components.

Alternatively, the body 16 of the neurostimulation device 10 is a chassis that is insertable into other headgear The body 16 enables the ultrasound probe 18 to be operably attached to or associated with a head containing the brain 14.

More precisely, the body 16 covers at least a portion of a subject's head and/or scalp, when worn by the subject 12. Head as used herein comprises the region from the top of the shoulder blades, including the neck region and at least the last two vertebrae of the top of the spine, the skull and jaw bones, the ears, and the tissues residing on and within, particularly the brain 14. The scalp is included within this region and refers to the area of the head where hair grows or where hair can be found in persons who are not bald, not including facial hair. When scalp is referred to, it refers to the region of the head from the forehead, behind the ears, and to the hairline dorsal to the face.

In addition, the body 16 is provided with a stereotaxic element to be able to move the ultrasound probe 18 at a desired location.

Alternatively or additionally, the body 16 is provided with a neuronavigation system.

According to the embodiments, the neuronavigation system encompasses at least one of a neuronavigator and computer program products devoted to computer-assist the movement of the ultrasound probe 18.

Description of the Ultrasound Probe 18

The ultrasound probe 18 is adapted to emit ultrasound pulses with a controllable ultrasound power.

Ultrasound refers to cyclical vibrations in a frequency range above human hearing, i.e., above about 20 thousand cycles per second (kilohertz, kHz) and including vibrational frequencies of tens and hundreds of millions of cycles per second (Megahertz, MHz), e.g., a range from about 0.02 MHz to 200 MHz.

In such specification, for instance, when applying a set of pulses, the ultrasound power is defined as the peak negative pressure. The ultrasound power is usually expressed in kiloPascal (kPa).

In the specific example, the ultrasound probe 18 comprises a plurality of transducers 22.

A transducer 22 is adapted to generate ultrasound waves.

According to the considered embodiment, the transducer 22 is an emitting transducer 22, a receiving and transmitting transducer 22, or a receiving transducer 22. The ultrasound transducers 22 are connected to the controller 20 for receiving data relative to the ultrasound pulses to apply. According to embodiments, the connection is wired or unwired.

The transducers 22 are driven by the controller 20.

For instance, each transducer 22 is a piezoelectric transducer, a piezopolymer transducer, composite transducers, gas matrix piezoelectric transducers or capacitive micromachined ultrasound transducers (also named after its abbreviation CMUT).

According to the described example, the transducers 22 are arranged in an array configuration.

In variant, the ultrasound probe 18 comprise only one transducer 22.

The ultrasound probe 18 is adapted to provide with ultrasound waves of any shape, notably focused or unfocused.

The ultrasound probe 18 is also adapted to generate ultrasound waves of any intensity.

The intensity of the acoustic beam is the amount of energy that impinges on a plane perpendicular to the beam per unit time divided by the area of the beam on the plane, and is given in energy per unit time per unit area, i.e., the power density per unit area, e.g., Watts per square centimeter ($W/cm^2$).

The intensity is, for instance, measured at the site of the brain 14 to be stimulated.

As a specific example, the ultrasound probe 18 is adapted to generate ultrasound wave with an intensity comprised between 0.0001 $mW/cm^2$ and 100 $W/cm^2$.

The ultrasound probe 18 is further adapted to generate ultrasound waves of any an ultrasound frequency.

In the described example, the ultrasound waves generated by the ultrasound probe 18 have an ultrasound frequency comprised between 0.02 MHz and 10.0 MHz.

As used herein, the cited intensities and frequencies are the intensity and frequency levels at the target tissue site, not the actual output number of the transducer 22.

For example, the pressure waveform experienced at the site of the target tissue would have a frequency below about 0.9 MHz and an intensity below about 900 $mW/cm^2$. The output of a transducer 22 may have to be much larger than the resulting effective amount at the target tissue site. For example, a transducer 22 may output 0.9 MHz ultrasound at about 90 W for transmission through an intact scalp and skull for the effective amount at the brain 14 tissues being stimulated to be about 0.9 MHz and below about 900 $mW/cm^2$, as the skull absorbs a significant portion of ultrasound waves.

Such properties enable to generate pulsed ultrasound waves for which a pulse repetition frequency can be defined.

According to one embodiment, the pulse repetition frequency is constant.

According to other embodiment, the pulse repetition frequency increases from a minimum value to a maximum value over a time interval called a ramp time.

Alternatively or in combination, the pulses generated may also vary according to other parameters of the pulse profile.

Notably, the cycles per pulse or the number of pulses may vary according to the embodiments.

Although pulses may be sine waves having a single ultrasound frequency herein, other oscillating shapes may be used, such as square waves, or spikes, or ramps, or a pulse includes multiple ultrasound frequencies composed of beat frequencies, harmonics, or a combination of frequencies generated by constructive or deconstructive interference techniques, or some or all of the aforementioned.

Description of the Controller 20

The controller 20 is represented as a separate system on FIG. 1.

However, the controller 20 may be within a helmet portion or built into a transducer 22.

The controller 20 is adapted to provide drive voltages and pulse patterns to one or more transducers 22, or to receive information from a remote or local component and using that information, drive one or more transducers 22.

More precisely, the controller 20 sends electrical commands (see dashed line 26 in FIG. 1) to electronic circuitry 24 which sends the drive voltages and pulse patterns to each transducer 22 as schematically indicated by dashed line 28 in FIG. 1.

As an example, the electronic circuitry 24 comprises an external trigger, a function generator and a power amplifier.

The controller 20 and a computer program product 30 are represented on FIG. 1. The interaction between the computer program product 30 and the controller 20 enables carrying out a method for setting parameters as will be described later. The method for setting parameters is thus a computer-implemented method.

The controller 20 is a desktop computer. In variant, the controller 20 is a rack-mounted computer, a laptop computer, a tablet computer, a PDA or a smartphone.

In specific embodiments, the computer is adapted to operate in real-time and/or is an embedded system, notably in a vehicle such as a plane.

In the case of FIG. 1, the controller 20 comprises a calculator 32, a user interface 34 and a communication device 36.

The calculator 32 is electronic circuitry adapted to manipulate and/or transform data represented by electronic or physical quantities in registers of the calculator 32 and/or memories in other similar data corresponding to physical data in the memories of the registers or other kinds of displaying devices, transmitting devices or memory devices.

As specific examples, the calculator 32 comprises a monocore or multicore processor (such as a CPU, a GPU, a microcontroller and a DSP), a programmable logic circuitry (such as an ASIC, a FPGA, a PLD and PLA), a state machine, gated logic and discrete hardware components.

The calculator 32 comprises a data-processing unit 38 which is adapted to process data, notably by carrying out calculations, memories 40 adapted to store data and a reader 42 adapted to read a computer readable medium.

The user interface 34 comprises an input device 44 and an output device 46.

The input device 44 is a device enabling the user of the controller 20 to input information or command to the controller 20.

In FIG. 1, the input device 44 is a keyboard. Alternatively, the input device 44 is a pointing device (such as a mouse, a touch pad and a digitizing tablet), a voice-recognition device, an eye tracker or a haptic device (motion gestures analysis).

The output device 46 is a graphical user interface, which is a display unit adapted to provide information to the user of the controller 20.

In FIG. 1, the output device 46 is a display screen for visual presentation of output. In other embodiments, the output device is a printer, an augmented and/or virtual display unit, a speaker or another sound generating device for audible presentation of output, a unit producing vibrations and/or odors or a unit adapted to produce electrical signal.

In a specific embodiment, the input device 44 and the output device 46 are the same component forming man-machine interfaces, such as an interactive screen.

The communication device 36 enables unidirectional or bidirectional communication between the components of the controller 20. For instance, the communication device 36 is a bus communication system or an input/output interface.

The presence of the communication device 36 enables, in some embodiments, the components of the controller 20 to be remote one from another.

The computer program product 30 comprises a computer readable medium 48.

The computer readable medium 48 is a tangible device that can be read by the reader 42 of the calculator 32.

Notably, the computer readable medium 48 is not transitory signals per se, such as radio waves or other freely propagating electromagnetic waves, such as light pulses or electronic signals.

Such computer readable storage medium 48 is, for instance, an electronic storage device, a magnetic storage device, an optical storage device, an electromagnetic storage device, a semiconductor storage device or any combination thereof.

As a non-exhaustive list of more specific examples, the computer readable storage medium 48 is a mechanically encoded device such a punchcards or raised structures in a groove, a diskette, a hard disk, a ROM, a RAM, an EROM, an EEPROM, a magnetic-optical disk, a SRAM, a CD-ROM, a DVD, a memory stick, a floppy disk, a flash memory, a SSD or a PC card such as a PCMCIA.

A computer program is stored in the computer readable storage medium 48. The computer program comprises one or more stored sequence of program instructions.

Such program instructions when run by the data-processing unit 38, cause the execution of steps of any method that will be described below.

For instance, the form of the program instructions is a source code form, a computer executable form or any intermediate forms between a source code and a computer executable form, such as the form resulting from the conversion of the source code via an interpreter, an assembler, a compiler, a linker or a locator. In variant, program instructions are a microcode, firmware instructions, state-setting data, configuration data for integrated circuitry (for instance VHDL) or an object code.

Program instructions are written in any combination of one or more languages, such as an object oriented programming language (FORTRAN, C"++, JAVA, HTML), procedural programming language (language C for instance).

Alternatively, the program instructions is downloaded from an external source through a network, as it is notably the case for applications. In such case, the computer program product comprises a computer-readable data carrier having stored thereon the program instructions or a data carrier signal having encoded thereon the program instructions.

In each case, the computer program product 30 comprises instructions, which are loadable into the data-processing unit 38 and adapted to cause execution of steps of any method described below when run by the data-processing unit 38. According to the embodiments, the execution is entirely or partially achieved either on the controller 20, that is a single computer, or in a distributed system among several computers (notably via cloud computing).

Description of Variants of the Neurostimulation Device 10

The neurostimulation device 10 may also comprise at least one acoustic lens.

An acoustic lens is adapted to interact with the ultrasound waves so as to, for instance, focus the waves onto a specific location of the subject 12.

As a specific example, the acoustic lens is made with one or several metamaterial.

Optionally, the neurostimulation device 10 may comprise other elements.

For instance, the other elements are any one of power sources, components for transmitting or receiving data, components for remote activation of the ultrasound transducers 22 or other components, global positioning components and other location or tracking components.

The neurostimulation device 10 may also be provided with other imaging or measuring elements, such as EEG or MRI.

As a specific example, one other elements is one or more cooling components incorporated into the body 16 of the device, or placed on the scalp before, during or after providing ultrasound waves to the head. A cooling component may be ultrasound transparent, so that the waveforms, intensity and/or frequency are not altered by the cooling component.

A cooling component may be an ice bag; a freezable container that is chilled by placing in a cold location, such as a freezer; a container of chemicals such that a chemical reaction can be initiated that is endothermic and cools the container; a mechanically chilled material or container which is cooled by mechanical means; or any other material or container known in the art that may provide a cool or cold surface that may be applied to the head of a subject 12.

Operating of the System

The operating of the neurostimulation device 10 is now described in reference to an example of carrying out a method for stimulating cerebral activity of a subject 12.

The method for stimulating comprises three phases: a first phase of measuring, a second phase of preparing and a third phase of applying.

During the first phase, the motor threshold excitation is measured.

By definition, the motor threshold excitation corresponds to the ultrasound power leading to 50% success of obtaining a motor response of the subject 12 when stimulating the cerebral activity of the subject 12 with the neurostimulation device 10.

This means that one excitation of the subject 12 over two excitation leads to a motor response of the subject 12 and that in such case, the motor threshold excitation is the value of the peak acoustic pressure.

As an example, the motor response can be evaluated by using electrode recording of the cerebral activity.

In an embodiment, each excitation is a pulse of 160 ms duration, each pulse being separated by a time span of 10 seconds.

A more detailed and specific layout of a specific embodiment can be found in the experimental section.

Therefore, at the end of the first phase, the motor threshold excitation is known.

The second phase is a phase of preparing the neurostimulation device 10 before stimulating cerebral activity of the subject 12.

In this phase, the neurostimulation device 10 is prepared without being used simultaneously to apply any ultrasound.

The second phase corresponds to a method of setting parameters of the neurostimulation device 10.

Such method of setting is a computer-implemented method.

This means that the method of setting is carried out by the controller 20.

The method of setting comprises a step of providing and a step of tuning.

At the step of providing, the motor threshold excitation is provided.

The motor threshold excitation is, for instance, received by the controller 20.

According to an embodiment, the information relative to the motor threshold excitation is sent via a network.

In another embodiment, the information is entered by the user in the controller 20 by using the input device.

The way the information is obtained is indifferent to the second phase. The use of the first phase is only an example of embodiment.

At the step of tuning, the parameters of the neurostimulation device 10 are set.

This means that the parameters of the neurostimulation device 10 are adjusted to the use case foreseen for the neurostimulation device 10.

The parameters of the neurostimulation device 10 are notably the parameters of the ultrasound probe 18.

For instance, the parameters of the neurostimulation device 10 are the ultrasound power of the pulses, the frequency of the applied pulses, the position of the ultrasound probe 18, the number of cycles during one application or the number of ultrasound applications per day.

At least one parameter of these parameters of the neurostimulation device is set based on the provided motor threshold excitation.

In the present example, the step of setting comprises setting the ultrasound power of the pulses so that the ratio between the ultrasound power of the pulses and the motor threshold excitation be superior to 1.2. Such ratio is named first ratio in what follows.

This ratio is implicitly limited by a maximal intensity. This maximal intensity is the value of the ultrasound power of the pulses above which damage or biological effects are induced in the brain area which is reached by the ultrasound.

In practice, the superior value of the ratio is set to a safety value which is inferior to the maximal intensity. Notably, such value is expressed by using the mechanical index which also depends from the frequency.

Preferably, in the current case, the ultrasound power of the pulses is set so that the ratio is inferior to or equal to 2.0.

This step of setting is, for instance, achieved by setting the electrical command of the ultrasound probe 18 to the desired value.

The same applies for each of the other parameters and is not repeated in what follows.

According to a preferred embodiment, the value of the ultrasound power of the pulses is set to a value of the first ratio comprised between 1.4 and 1.8, preferably between 1.55 and 1.65.

The present step of setting also comprises a step of setting the frequency.

The frequency is set between 400 kilohertz (kHz) and 600 kHz, preferably between 450 kHz and 550 kHz, more preferably between 490 kHz and 510 KHz.

The present step of setting also comprises a step of setting the position of the ultrasound probe 18.

The position of the ultrasound probe 18 is set so that the ultrasound pulses be applied in the infralimbic cortex of the subject 12.

The present step of setting further comprises a step of setting the number of cycles per application.

By definition, the number of cycles is the number of pulses applied during one application of the ultrasound pulses.

The number of cycles is set to be comprised to a value between 75000 and 80000, preferably between 78000 and 82000 and more preferably between 79000 and 81000.

The present step of setting also comprises a step of setting the number of ultrasound applications in one day.

By definition, an ultrasound application is a sequence of a set of uninterrupted ultrasound pulses.

The number of ultrasound applications in one day is the number of ultrasound applications to which a subject can be exposed safely. Such number of ultrasound applications in one day is often given by a norm ensuring safety for human beings exposed to ultrasounds.

The number of ultrasound applications is set to a value between 40 and 60, preferably between 45 and 55 and more preferably between 48 and 52.

During the third phase, the ultrasound waves are applied in accordance with the parameters set at the second phase.

The application corresponds to a stimulation of the brain 14 activity which can also be named as neuromodulation or neuronal activation. Such technique refers to invasive or non-invasive techniques to alter the excitability, action potential rate, vesicular release rate, or other biochemical pathway in neurons or other cell types in the brain 14.

Such method is a method that can be used to treat a neuropathological illnesses and/or disorders.

Neuropathological illnesses and/or disorders encompass Parkinson's disease, Alzheimer's disease, coma, epilepsy, stroke, depression, schizophrenia, addiction, neurogenic pain, cognitive/memory dysfunction, diabetes, obesity, obsessive compulsive disorders, traumatic brain injury, post-traumatic stress disorder (PTSD), minimally conscious or vegetative states, locked in syndrome, spinal cord injuries, peripheral neuropathies, migraine and epilepsy.

By the word "treating", it is referred to inhibiting, preventing, curing, reversing, attenuating, alleviating, minimizing, suppressing or halting the deleterious effects of a disease and/or causing the reduction, remission or regression of a disease.

Such method is a method that is particularly appropriate to be used for treating a mood-related illness, such as the depression.

The proposed method is also well adapted to be used to deal with anxiety-like behaviors of the subject 12, notably stress of the subject 12.

The proposed method can also be used for non-therapy methods, such as to modulate emotion of the subject 12.

By the term "emotion", it is meant one or a plurality of emotions or a mood or emotional state.

The emotions are chosen from the following non-exhaustive list: affection, anger, angst, anguish, annoyance, apathy, arousal, awe, boldness, boredom, contempt, contentment, curiosity, non-clinical depression, desire, despair, disappointment, disgust, dread, ecstasy, embarrassment, envy, euphoria, excitement, fear, fearlessness, frustration, gratitude, grief guilt, happiness, hatred, hope, horror, hostility, hurt, hysteria, indifference, interest, jealousy, joy, loathing, loneliness, love, lust, misery, passion, pity, pleasure, pride, rage, regret, remorse, sadness, satisfaction, shame, shock, shyness, sorrow, suffering, surprise, terror, wonder, worry, zeal, and zest.

Such method for modulation can produce applicable acute or long-term effects.

According to embodiment, the above-described methods can be implemented in many ways, notably using hardware, software or a combination thereof. In particular, each step is implemented by a module adapted to achieve the step or computer instructions adapted to cause the execution of the step by interaction with the controller 20 or a specific neurostimulation device 10 comprising the controller 20.

It should also be noted that two steps in succession may, in fact, be executed substantially concurrently or in a reverse order depending on the considered embodiments.

Experimental Results

General Summary

Nowadays, major depression is treated with antidepressants but 50% of patients do not show improvement after treatment: they are non-responders or resistant. Alternative therapies include transcranial magnetic stimulation or deep brain 14 stimulation, but these techniques have various limitations.

Ultrasound neurostimulation has been recently introduced as a physical non-invasive method for brain 14 tissue stimulation and has gained increasing interest.

In the present section of the patent application, it is sought to evaluate the efficiency of transcranial ultrasound neurostimulation at 0.5 MHz in an unpredictable chronic mild stress (UCMS) mouse model.

The acoustic parameters that can reliably stimulate the primary motor cortex in mice are identified and a pattern of repeated acoustic stimuli that induce neural activation of the infralimbic cortex and not in the adjacent areas of the brain 14 is established.

Then, ultrasound neurostimulation was applied chronically to the infralimbic cortex in unpredictable chronic mild stress mouse mice.

To assess the efficacy of ultrasound neurostimulation, behavioral tests were performed on treated and control mice and compared to mice treated with fluoxetine, a classic antidepressant. In addition, micro-positron emission tomography imaging (named micro-PET imaging in what follows) and metabolomic analyses were performed to assess the effects of ultrasound neurostimulation on brain 14 regions.

The results suggested that ultrasound neurostimulation alleviates UCMS-induced anxiety-related behaviors while fluoxetine acted on depressive-like behaviors.

Ultrasound neurostimulation also modified the brain 14 metabolism in different brain 14 regions as depicted by microPET imaging with using a contrast agent such as fludeoxyglucose ($^{18}F$) (named FDG in what follows).

Furthermore, metabolomic analyses demonstrated that several pathways in cortical and subcortical regions were affected by ultrasound neurostimulation.

However, no change appeared in hippocampal cell proliferation or neurogenesis.

In conclusion, our selected ultrasound settings might counteract specific behavioral modifications elicited by the UCMS model.

INTRODUCTION

According to the World Health Organization, major depression has already become the second most prevalent cause of illness-induced disability, which makes this disorder one of the main contributors of the Global Burden of Disease. It is generally treated with chronic antidepressants, which consist of drugs increasing monoaminergic neurotransmission such as selective serotonin reuptake inhibitors.

However, nearly 65% of the patients do not respond to this first-line therapy, and it is established that 30-50% of patients are resistant to chronic antidepressants, meaning they do not show remission after treatment with several chronic antidepressants: this condition is conventionally referred to as treatment resistant depression.

Recently, treatment of treatment resistant depression has involved neurostimulation, which consists in activating/inhibiting the cerebral networks whose functioning is modified in major depression.

Regions of interest include the dorsolateral prefrontal cortex, the subgenual part of the anterior cingulate cortex, the nucleus accumbens or the lateral habenula.

The anterior cingulate cortex is the frontal part of the cingulate cortex that resembles a "collar" surrounding the frontal part of the corpus callosum. It consists of Brodmann areas 24, 32, and 33. It appears to play a role in a wide variety of autonomic functions, such as regulating blood pressure and heart rate. It is also involved in rational cognitive functions, such as reward anticipation, decision-making, empathy, impulse control, and emotion.

While the dorsolateral prefrontal cortex is a cortical area that can be targeted using neurostimulation methods such as repeated transcranial magnetic stimulation or direct current stimulation, the same does not apply to deeper brain 14 areas that can be targeted only using invasive approaches such as deep brain stimulation.

Therefore, it is desirable to develop novel and efficient neurostimulation techniques that can target deep brain 14 areas in a focal and non-invasive manner.

Ultrasound technology has been evaluated as a therapeutic tool in neurology/psychiatry either to induce non-invasive surgical ablation of a given brain 14 region, to potentiate drug delivery, or more recently, to induce neuromodulation of a specific brain 14 area.

Ultrasound neurostimulation offers the advantages of being focused and able to activate deep regions of the brain 14, which is quite relevant to treat psychiatric disorders. However, ultrasound neurostimulation has yet to be evaluated for this indication.

In this context, the objective of this section is to assess whether repeated transcranial ultrasound neurostimulation of the infralimbic cortex, the rodent's equivalent of the anterior cingulate cortex can counteract modifications induced by the UCMS procedure in mice.

The UCMS model is considered a naturalistic model of major depression as it satisfies some criteria for face, predictive, and construct validity.

The angular cingulate cortex was selected as a relevant target region for the following reasons:
  its activity pattern has been shown to be modified in patients suffering from major depression,
  repeated deep brain stimulation of angular cingulate cortex elicited therapeutic effects in treatment resistant depression patients,
  using a mouse model, it has been observed in a previous study that UCMS elicited changes in gene expression in this region that were partly reversed by chronic treatment with fluoxetine, a selective serotonin reuptake inhibitor, deep brain stimulation of this region in mice induced therapeutic-like effects in the UCMS model.

Optimal ultrasound parameters were first assessed by evaluating motor response after stimulation of the contralateral primary motor cortex, which were then used to investigate the effects of repeated ultrasound neurostimulation targeted to the infralimbic cortex. This was achieved using a 5-week UCMS model combined with a behavioral analysis, FDG micro-PET imaging and a metabolomic analysis.

Experiments

BRIEF DESCRIPTION OF THE FIGURES

FIGS. 2 to 12 are now briefly presented. For more details about the described elements, please refer to the corresponding paragraphs in what follows.

Figure 2:
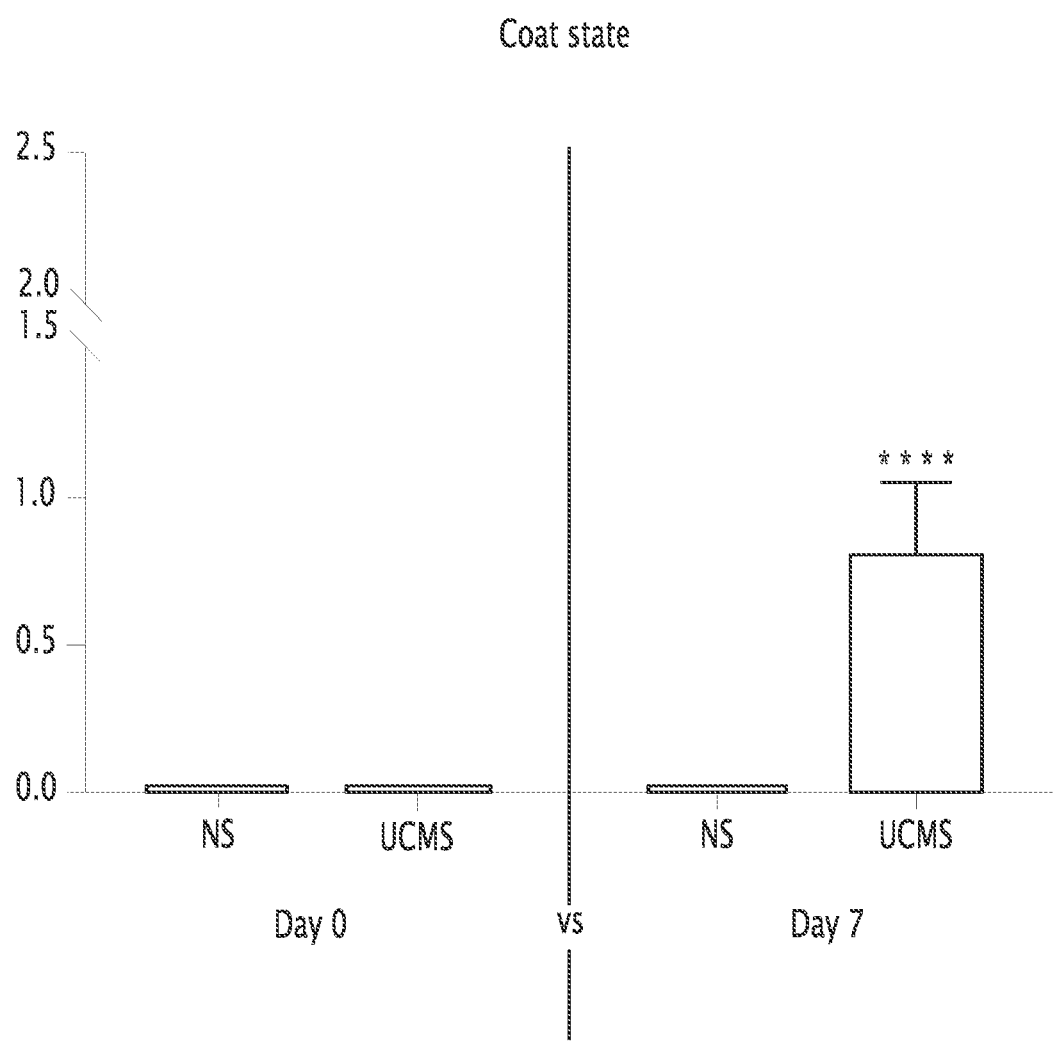
FIGS. 2 to 12 are representations relative to the experimental section, a more precise description of these figures can be found in this section.

FIG. 2 is a graph presenting the coat state evolution from day 0 to day 7. The deterioration of the fur/grooming behaviors is expressed a score between 0 (minimum) and 2.5 (maximum). The UCMS regimen significantly increased the coat state at day 7 of the procedure compared to non-stressed mice (t(63)=11, p<0.0001). NS means non-stressed; and **** means p<0.0001.

Figure 3:
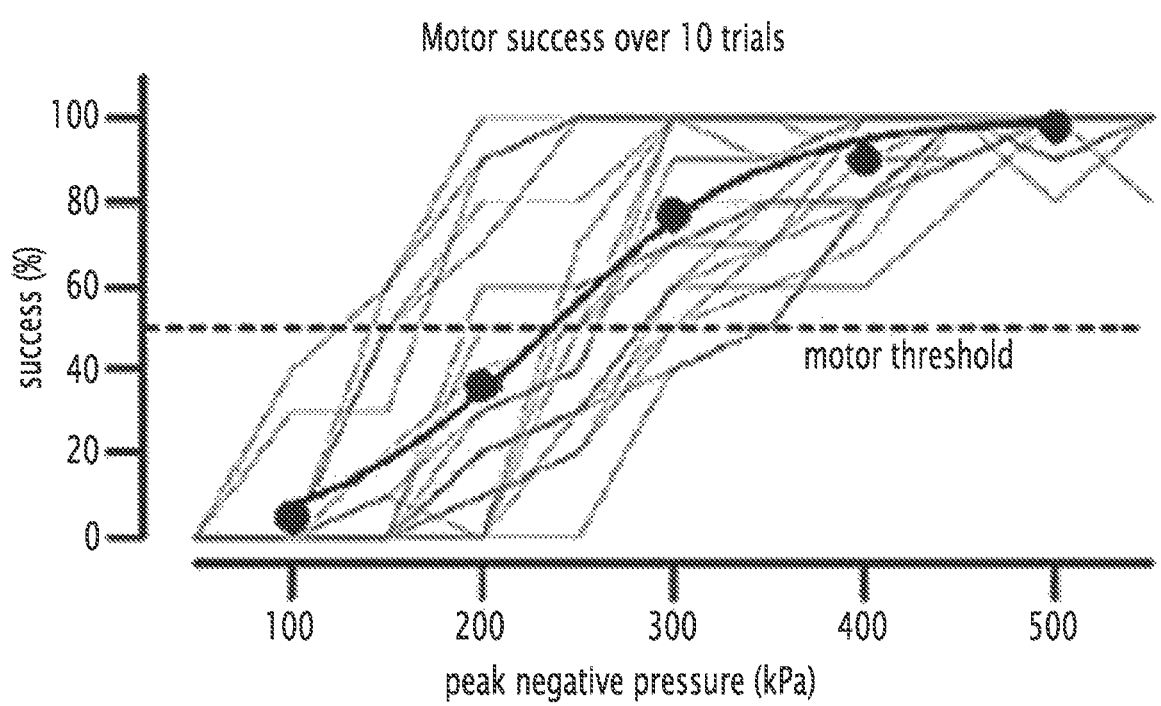

FIG. 3 is a graph presenting the value of motor success in % in function of the peak negative pressure expressed in kPa. Motor responses were evaluated at 0.1% isoflurane gaseous anaesthesia with electrode-free recordings. Each mouse was tested for the full range of pressures (50 to 500 kPa, red lines) and each step was assessed with twelve trials, which gave a mean percentage of success for a given pressure (black dots). The motor threshold excitation was then defined as the pressure that produced 50% motor success (dashed black line), visible on the sigmoid threshold function (plain black line) fitted using a Boltzmann equation.

Figure 4:
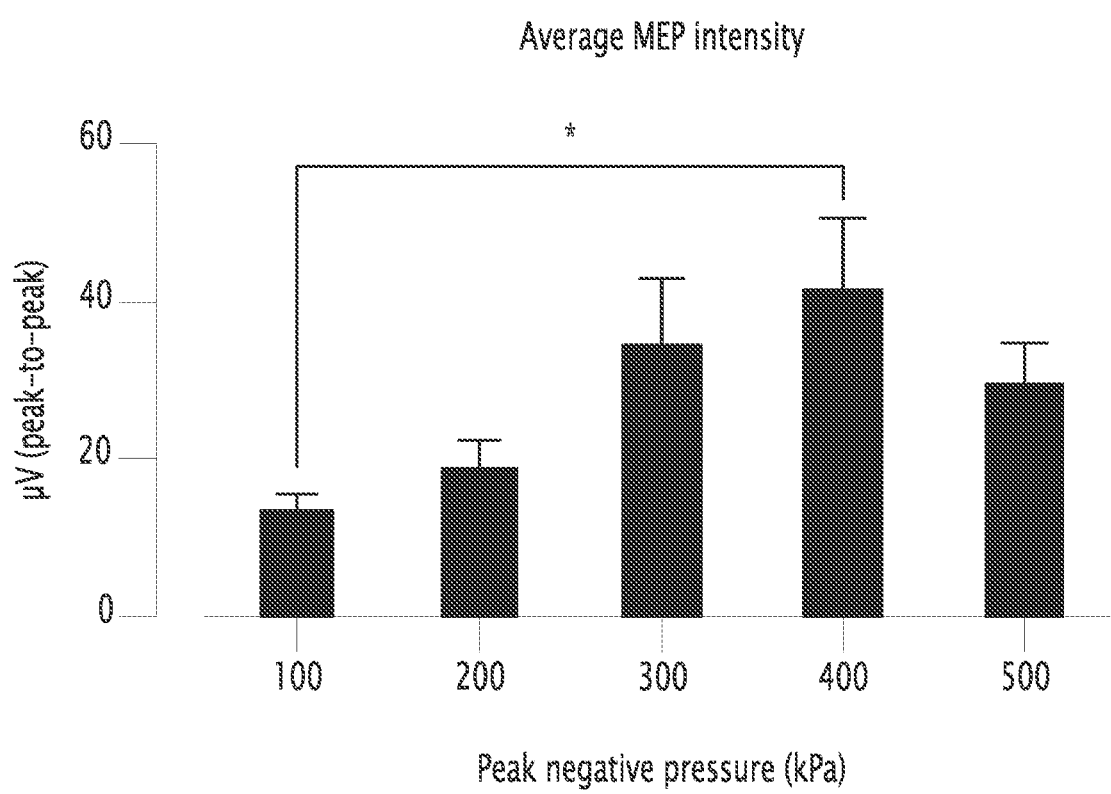

FIG. 4 represents the evolution of tension in function of the peak negative pressure expressed in kPa. At 1% isoflurane gaseous anaesthesia, motor evoked potentials (MEP) intensities are recorded with subdermal electrodes: an active in the brachioradialis muscle group (red) and a reference between the third and fourth carpometacarpal joints (black). Two-by-two comparisons: * p<0.05.

Figure 5:
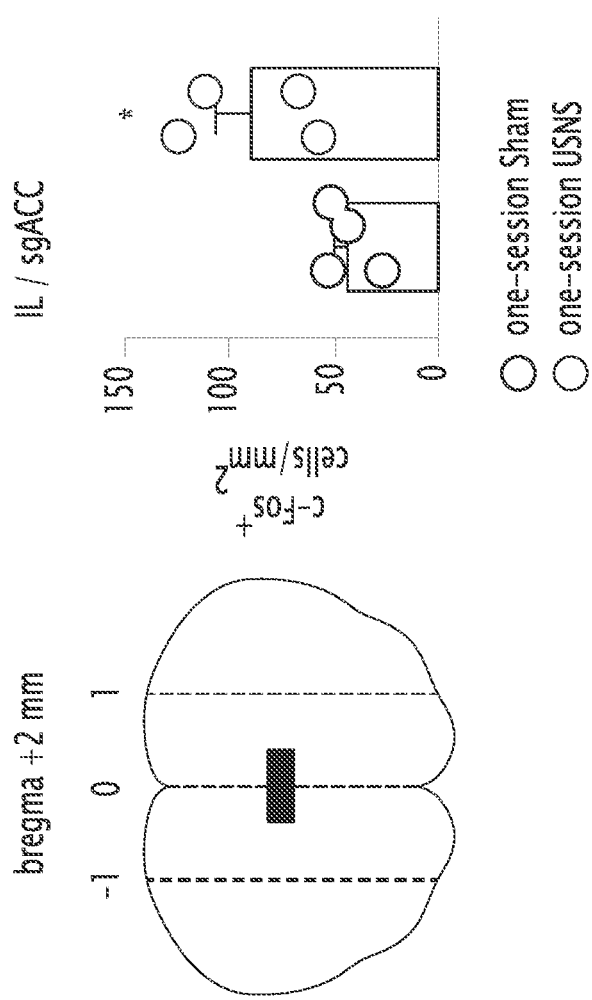

FIG. 5 represents the location of the ultrasound probe 18 (left part of the figure) and, on the right part of the figure, the obtained c-Fos induced by one session of ultrasound neurostimulation at bregma +2 mm (one-session Sham: left, one-session ultrasound neurostimulation: right).

Figure 6:
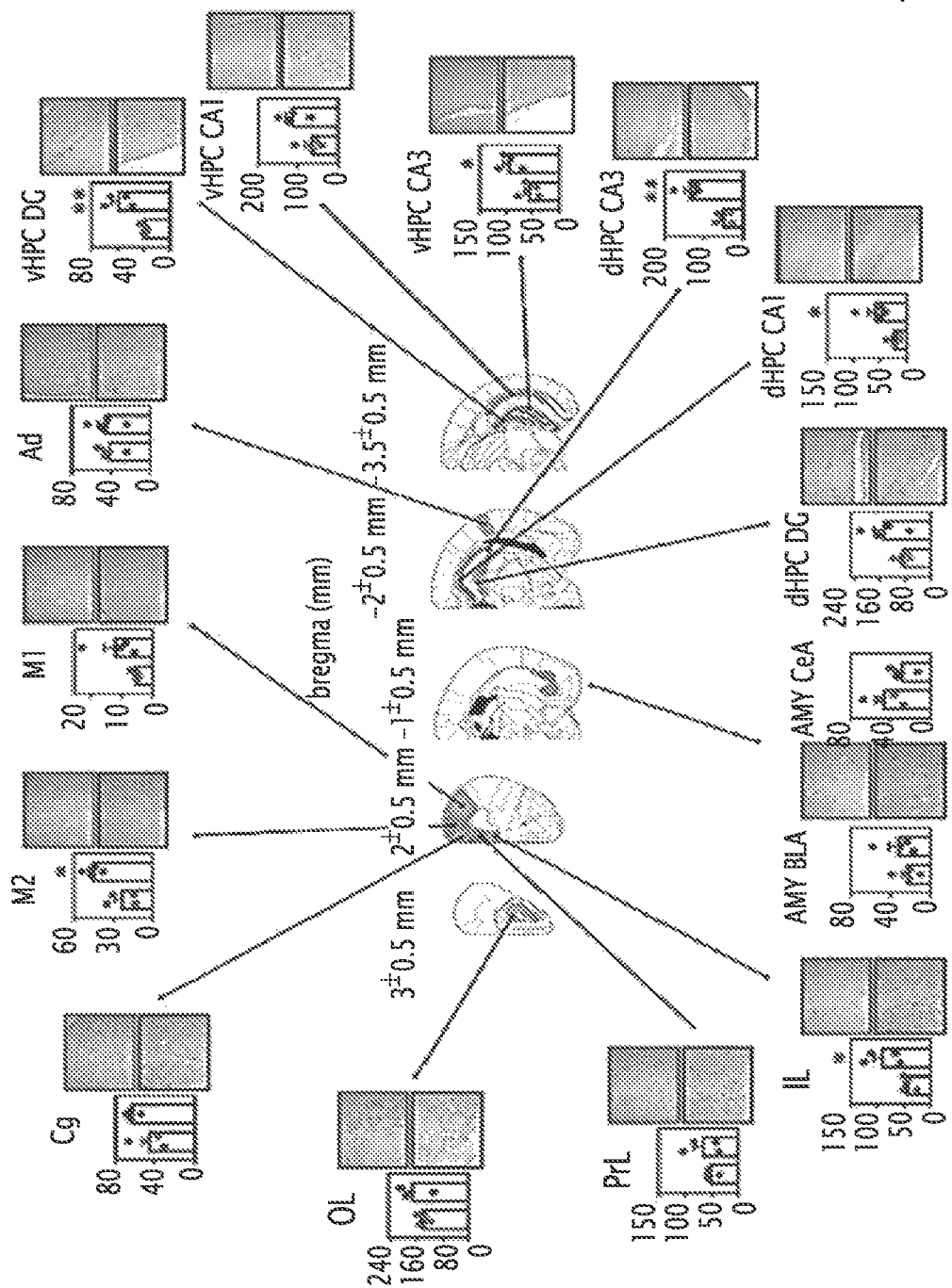

FIG. 6 represents the detailed results of c-Fos immunolabelling following one-session USNS. Ordinates represent c-Fos+ cells/mm². Ad: auditory cortex, AMY: amygdala, BLA: basolateral amygdala, CeA: central amygdala, Cg: anterior cingulate cortex, DG: dentate gyrus, dHipp: dorsal hippocampus, IL: infralimbic cortex, M1: primary motor cortex, M2: secondary motor cortex, OL: olfactory areas, PrL: prelimbic cortex, vHipp: ventral hippocampus.

Figure 7:
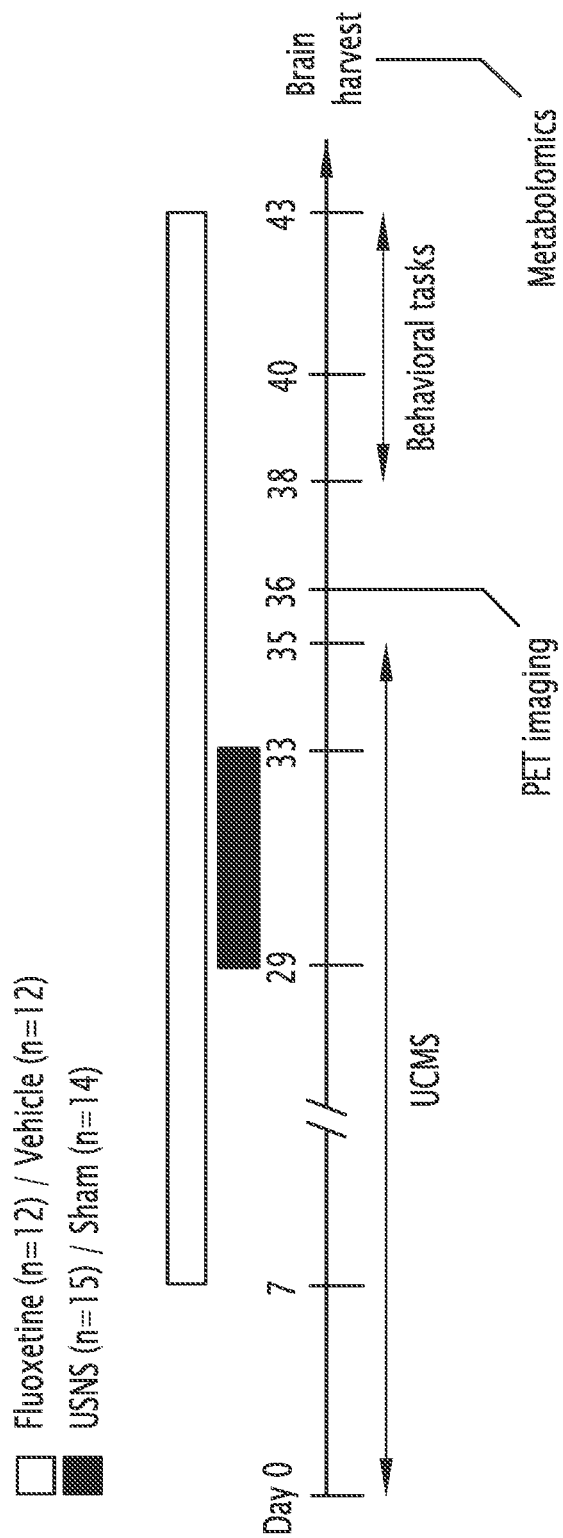
Figure 8:
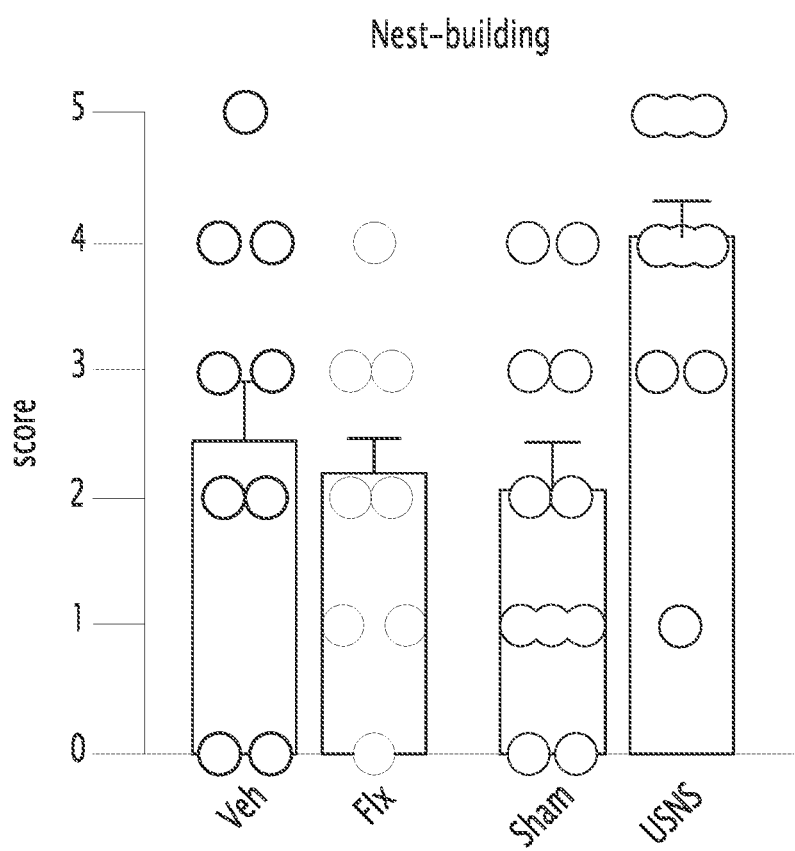

FIG. 7 corresponds to an experimental time line for several cases. In this figure *p corresponds to a value of p strictly inferior to 0.05.

Figure 9:
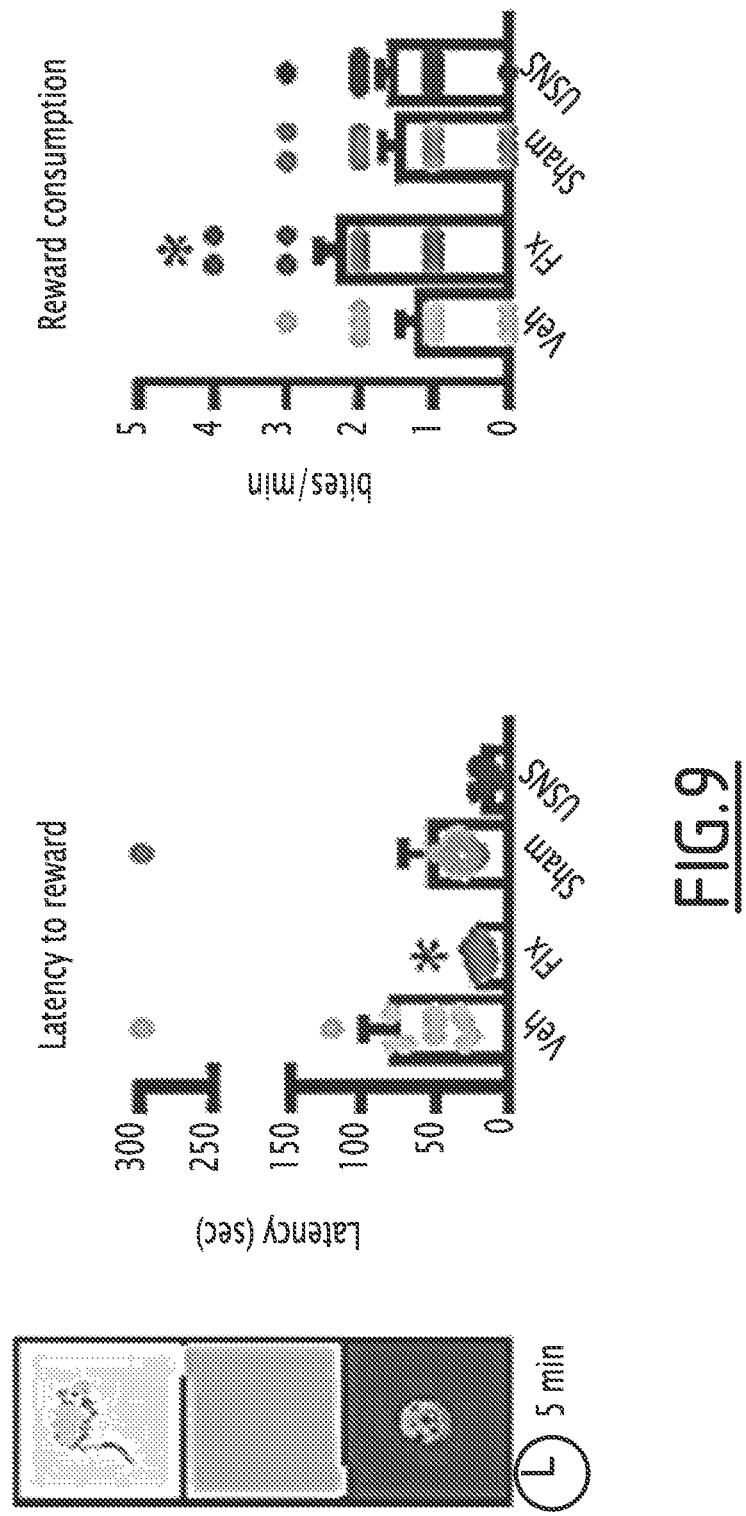
Figure 10:
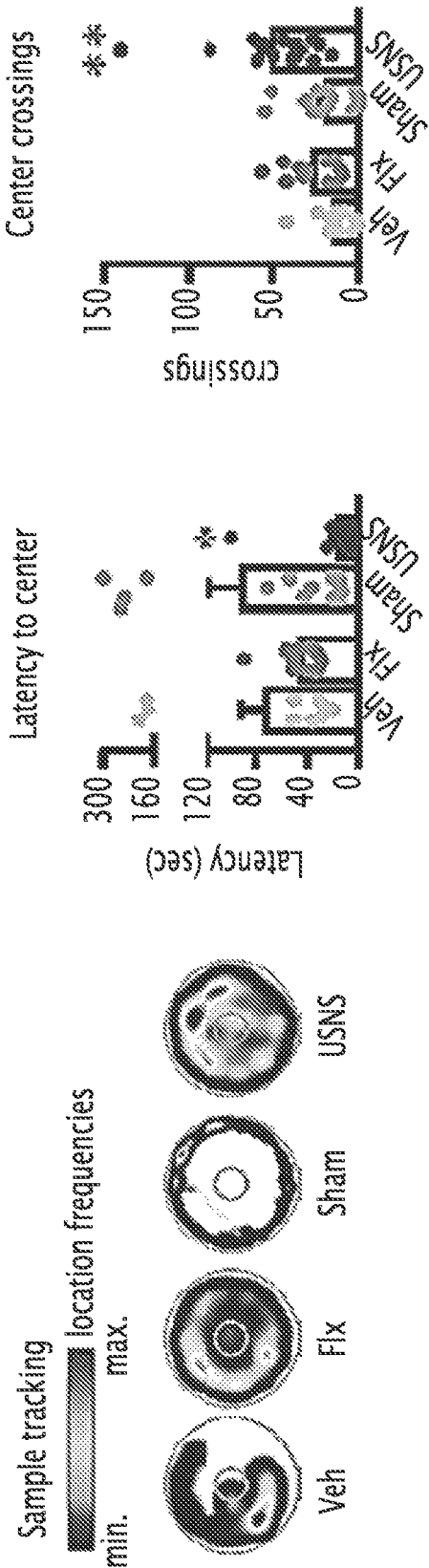
Figure 11:
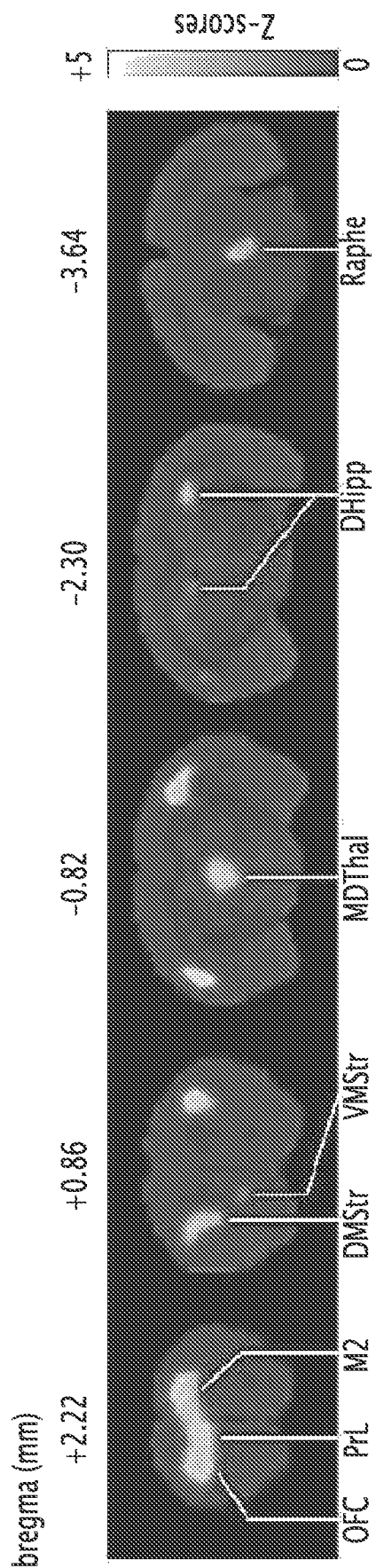

FIGS. 8 to 11 illustrates the case of in vivo measurements for several behaviours. The graph of FIG. 8 corresponds to the case of nest-building score with scale ranging from 1 to 5. The graphs of FIG. 9 are relative to the reward-maze test apparatus and behavioral measures (the left one concerns the latency to reward while the right one concerns the reward consumption). FIG. 10 deals with open-field task. Heat maps of the relative position in the arena for one representative individual of each group and behavioral measures: latency to the center and center crossing (count, #). FIG. 11 is a set of FDG microPET images obtained for several bregma and showing the Z-scores for the following regions: orbitofrontal cortex, prelimbic cortex, secondary motor area, dorsomedial striatum, ventromedial striatum, MDThal, dorsal hippocampus, raphe. Data are expressed as mean±SEM. Two-by-two comparisons: * refers to p<0.05 and ** refers to p<0.01.

Figure 12:
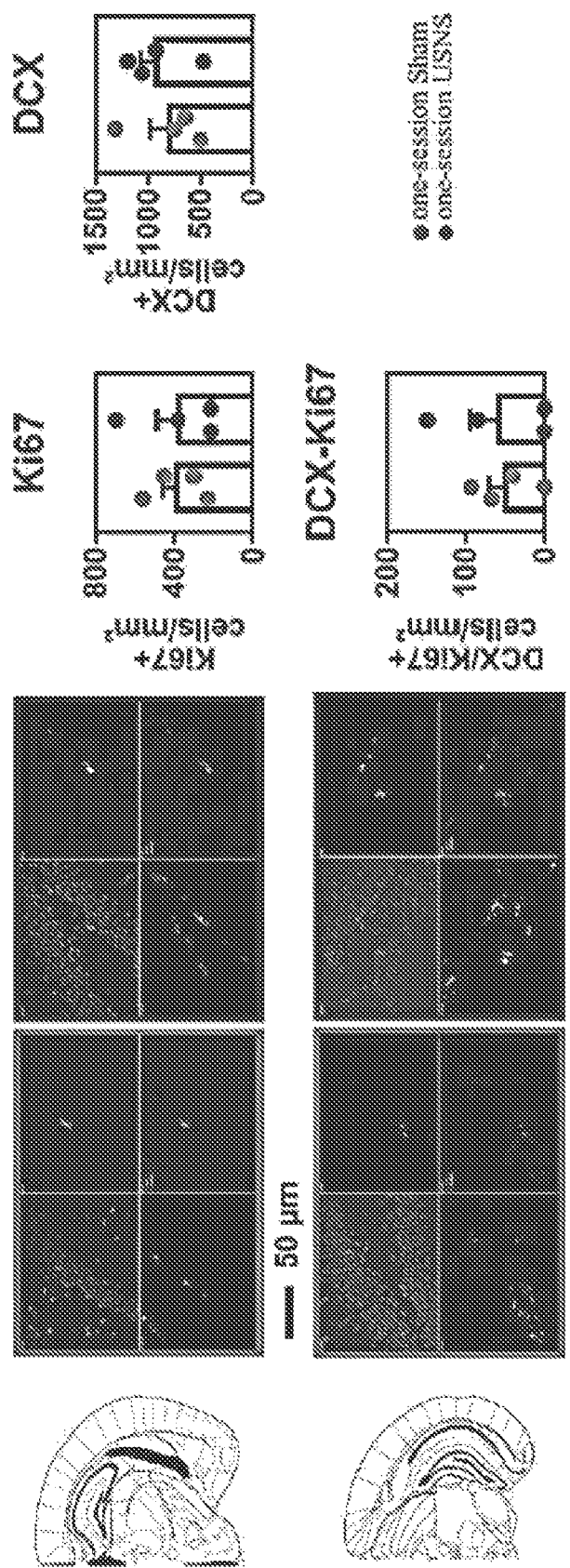

The representation of FIG. 12 correspond to newborn neurons and proliferating cells in the dentate gyrus of the hippocampus following chronic ultrasound neurostimulation treatment.

Protocol of the Experiments

Experimental Layout

Eighty-three male BALB/cByJRj mice were obtained from Janvier Labs (Le Genest-Saint-Isle, France), aged 9 weeks (29±1.5 g) at the beginning of the experiments. Animals were housed in standard condition (12:12 light-dark cycle, room temperature 22±2° C., free access to food and water).

Thirty mice were used for setting-up ultrasound stimulation parameters with motor response measurements, determined with: 1) electrode-free video recordings of the targeted limb (n=20) and 2) electromyography (n=10).

The remaining cohort (n=53) was divided in four distinct treatment groups (Veh, Flx, Sham, ultrasound) that underwent 35 days of the unpredictable chronic mild stress regimen (UCMS) to induce depressive-like behaviors.

Mice were semi-randomized and distributed into experimental groups based upon their coat state, significantly deteriorated by the UCMS regimen at day 7.

The coat state score, which reflects the deterioration of the fur/grooming behaviors, is a common measure of the depressive-like phenotype: the coat state of UCMS mice (n=53) was compared to the coat state of non-stressed mice (n=12) at day 0 and day 7 (see FIG. 2).

More precisely, it can be seen in FIG. 2 that the deterioration of the fur/grooming behaviors is expressed a score between 0 (minimum) and 2.5 (maximum). The UCMS regimen significantly increased the coat state at day 7 of the procedure compared to non-stressed mice (t(63)=11, p<0.0001).

At day 0, UCMS mice were randomly picked from cages of 7-8 naive individuals; thus, nonstressed mice came from the same housing and displayed no difference from UCMS mice in terms of age (9 weeks) or weight (29.5 g ±1.2 g).

From day 7 on, mice from the Veh (vehicle) and the Flx (fluoxetine) groups were chronically treated through drinking water respectively with water alone (n=12) or 15 mg/kg fluoxetine (n=12).

Each day from day 29 to day 33, mice from the ultrasound neurostimulation and the Sham groups were either treated with repeated ultrasound neurostimulation under 1% isoflurane gaseous anaesthesia (n=15) or solely anesthetized (n=14).

The whole cohort underwent behavioral tasks from day 38 to day 43 to test for depressive-like and anxiety-related behaviors. To assess the underlying mechanisms, it was decided to focus on a subset of mice (n=10/group) of the Sham and ultrasound neurostimulation groups.

At day 36, ultrasound neurostimulation mice were scanned with [18F]-FDG microPET imaging and compared to Sham mice.

At day 43, brains 14 were harvested to observe metabolome changes that occurred in ultrasound neurostimulation (n=8/group) and Sham mice (n=8/group).

Animals that went for metabolomics were also scanned with microPET imaging. All experiments were compliant with Directive 2010/63/EU guidelines on animal ethics.

Brain Stimulation Setup

The stimulation setup makes use of the neurostimulation device 10, which was described in reference to FIG. 1.

Ultrasound stimuli were generated using a 500 KHz single-element transducer 22 focused at 65 mm (active diameter of 38 mm, Imasonic, Besançon, France). The acoustic pressure measured in a degassed water tank using a calibrated hydrophone (HGL 200, ONDA, Sunnyvale, CA, USA) positioned at the focus. The attenuation coefficient of mice skulls (n=7) was estimated ex vivo using standard through-transmission insertion loss technique. At 500 kHz, the attenuation coefficient was 6.32±2.18% (mean±SD), and used to derate the acoustic pressure inside the brain 14.

The transducer 22 was positioned on the mouse brain 14 with an appended plastic column, filled with degassed water. A distal collimator of 10 mm was sealed with polyethylene and coupled with centrifuged ultrasound gel to the shaved cranium of the animal. Throughout most ultrasound procedures, mice were anesthetized with 1.8 litres per minute gaseous isoflurane (2.5% induction, 1% maintenance; halogenated ether, Aerrane, Baxter SAS), placed in a stereotaxic frame (SM-6M-HT, Narishige), the head fixed with auxiliary ear bars (EB-5N, Narishige), while the transducer 22 column was operated by a custom-made 3-axis stereotaxic manipulator. Electrical signal was generated from a function generator (Agilent, Santa Clara, CA, USA) and then amplified using a power amplifier (ADECE, Artannes sur Indre, France).

c-Fos Analysis of Acute Ultrasound Neurostimulation

Mice were sacrificed 90 min after one session of ultrasound neurostimulation or one session of anaesthesia (1% isoflurane), which corresponds to a peak of c-Fos expression in the stimulated neurons. After a classic immunolabelling of the c-Fos protein in 40-μm coronal sections, the cellular densities (c-Fos+ cells/mm$^2$) were quantified on the targeted region (infralimbic cortex, infralimbic cortex) and its close surroundings (olfactory areas, OL; prelimbic cortex, PrL; anterior cingulate cortex, Cg; primary motor cortex, M1 and secondary motor cortex, M2) by an investigator blind to the experimental groups. In addition, distant connected areas were observed: the amygdala and the hippocampus.

Unpredictable Chronic Mild Stress

The main cohort of fifty-three mice followed the UCMS regimen from day 0 to day 35, as described previously. Briefly, mice were isolated in 24×11×12 cm cages without environmental enrichment and submitted to daily random socio-environmental stressors including: exposition to another mouse bedding, removal of sawdust, contention and light dark cycle perturbations. Mice were semi-randomized and distributed into experimental groups based upon their coat state, significantly deteriorated by the UCMS regimen at day 7.

Treatments

Pharmacological treatments (15 mg/kg fluoxetine) were given from day 7 on to achieve chronic administration at week 5. The chronic ultrasound neurostimulation treatment was given during the fifth week of the UCMS (stressors: 08:00-12:00 AM, treatment: 02:00 PM). To perform ultrasound neurostimulation, another function generator (Agilent, City, CA, USA), called external trigger, was used to control the repetition rate of the ultrasound stimulus defined in the motor cortex stimulation procedure. A 5 Vpp square wave, set to 0.1 Hz, was used to trigger the main function generator, set for 80,000 cycles of a sine wave (500 kHz). The pattern was repeated for 10 min (60 ultrasound stimuli) every 10 s. This constituted one treatment session of ultrasound neurostimulation, applied for 5 consecutive days from day 29 to day 33. The collimator was positioned close to midline at bregma +2 mm, a region that comprises the infralimbic cortex (infralimbic cortex), the rodent's equivalent of the anterior cingulate cortex connectivity-wise.

Behavioral Measures

Behaviors were assessed during the dark phase of the light-dark cycle, i.e., the active, awoken phase for the animals. The effects of ultrasound neurostimulation were assessed against those of the fluoxetine treatment from day 38 to day 43 with 1) the nest-building test, 2) the reward-maze test and 3) the open field task.

1. For the nest-building task, mice were moved on day 37 to Makrolon type III cages, then at 07:30 am of day 38, a square pressed cotton (5 cm$^2$) was placed on the sawdust. After 5 hours in standard condition, the state of the nest, built in cotton, was scored on a predefined scale. The mice were then put back in their smaller home cage.

2. To test for anhedonic traits, mice were subjected to a reward-maze test. The palatable value of the reward was induced by giving a sample every day to the animals from week 2 to week 3. To minimize environmental neophobia, mice were habituated three times to the paradigm on week 4 and the test was done under red light. The apparatus was made of three consecutive chambers (20×20×20 cm) growing darker in color (light gray to black). Common food pellets were removed from the cage lid 1 hour before the test. The mouse was placed in the light chamber and the reward at the centre of the black one. The latency to reach the reward and its consumption were measured for up to 5 min.

3. To test for anxiety-related behaviors, mice were subjected to the open-field task on day 43. Mice were placed in a brightly lit (200 lux) circular 33-centimeter (cm) wide open-field. The latency to reach the center area (d=10 cm) and the number of center-crossings were measured for up to 5 min. The movements of the mice were recorded and tracked with the software EthoVision XT (Noldus Information Technology, Netherlands) to generate individual heat maps, color-coded for position frequencies over the duration of the test.

Brain Imaging

Local uptake of FDG reflects cerebral metabolic rates of glucose utilization and allows the investigation of regional brain 14 metabolic status. Metabolic imaging using FDG was performed under basal conditions at day 36 of the procedure, with the mice fasted overnight before each scan.

The day of brain-imaging acquisition, awake mice were injected with FDG (18.5 MBq/100 g i.p.; Cyclopharma, Tours, France), and placed in their home cage for 45 min. Then, animals were anesthetized using isoflurane 4% (Baxter, Maurepas, France), placed on a heating pad (Minerve, Esternay, France) and centered in the field of view of the Explore VISTA-CT microPET camera (GE Healthcare, Velizy, France). A CT-scan was performed for attenuation correction of PET images and a list-mode PET acquisition of 30 minutes started 60 min after FDG injection. After data reconstruction using a 2-D OSEM algorithm, all images were co-registered and normalized for tissue activity in the whole brain 14. Quantitative results were expressed as mean±SD and were presented on Z-score maps using an array of regions of interest already defined in PMOD v3.2 software (PMOD Technologies Ltd, Switzerland).

During the experiments, the respiratory rate and body temperature of each animal were monitored and kept as constant as possible (70 respirations per minutes and 37° C., respectively). List-mode scans were rebinned into 6 frames of 300 sec, corrected for randoms, scatter and attenuation, and images were reconstructed using a 2-D OSEM algorithm (GE Healthcare, Velizy, France) into voxels of 0.3875×0.3875×0.775 mm3.

Data summed over the entire acquisition were used for image registration. Since brain anatomy is very similar for mice of similar weight, registration was accomplished as a rigid body transformation, with no warping or scaling. Each summed scan was individually smoothed with a Gaussian filter to improve the signal-to-noise ratio and to reduce the bias of misregistration into template space. For this smoothing, a kernel of 0.6×0.6×0.6 mm3 FWHM was used.

Each scan was coregistered using PMOD v3.2 software (PMOD Technologies Ltd, Switzerland) to a FDG PET template in Paxinos coordinates using a mutual information similarity function with Powell's convergence optimization method. The results were visually checked for misregistration. Each summed image was also used for statistical analysis. The regions of interest (ROI) atlas of Mirrione in Paxinos coordinates were merged to create a whole brain mask (WBM). To normalize the FDG uptake, tissue activity was divided by the whole brain 14 activity, calculated as the average activity in the WBM. Prior to statistical analysis, the WBM was applied over all PET scans to exclude extracerebral areas. The signals extracted using the ROIs on the Z-score maps were considered for further analysis when representing at least 50 contiguous voxels for a statistical threshold set at $p<0.05$.

Metabolomics

After brain 14 harvest at day 43, the anterior cingulate cortex (Cg), the prelimbic/infralimbic cortex (PrL/infralimbic cortex), the amygdala and the hippocampus were dissected and assessed for metabolomic analyses. This study was carried out by cerebral region analysis campaigns with a targeted metabolomic approach using LC-HRMS as an analytical platform (Q-Exactive, ThermoFisher). The brain 14 metabolome of Sham mice was compared with ultrasound neurostimulation mice (n=8/group).

More precisely, each sample was first lyophilized and then weighed precisely in order to finally normalize the results to the dry mass of tissue. Metabolites were then extracted from approximately 1-3 mg of tissue by two successive extractions, after homogenization, with a mixture of methanol/water (1/1, 0.75 mL). After centrifugation, the supernatant was collected, and the solvent evaporated by means of a speedvac. The dry residues were finally taken up in 150 µL of MeOH/$H_2O$ (1/1). 10 µL extracts of each sample were pooled to obtain a mixture used as a quality control. Finally, 20 µL were used for LC-HRMS analysis. Fifteen quality control (QC) samples were injected to equilibrate the chromatographic system before each analyses batch. The running order of samples was randomized, and QCs were analyzed every 10 samples. The autosampler temperature (Ultimate WPS-3000 UHPLC system, Dionex, Germany) was set at 4° C. and the injection volume for each sample was 5 µL.

For the chromatographic part (UPLC Ultimate WPS-3000 system Dionex, Germany), we used a C18-XB column (1.7 m, 100 Å, 150×2.1 mm) maintained at 40° C. A mixture of two solvents was used (Solv A: H2O+0.1% formic acid, Solv B: MeOH+0.1% formic acid) at a flow rate of 0.4 mL/min. The gradient used for the two ionization modes is as follows: 0 to 2 min (A: 99.9%, B: 0.1%); 2-6 min (A: 75%, B: 25%); 6 to 10 min (A: 20%, B: 80%); 10 to 12 min (A: 10%, B: 90%); 12 to 23 min (A: 0.1%, B: 99.9%); 23 to 26.5 min (A: 99.9%, B: 0.1%).

HESI (heated electrospray ionization) source parameters were, for both modes, a spray voltage of 3 kV, capillary temperature of 325° C., heater temperature of 325° C., sheath gas flow of 35 arbitrary units (AU), auxiliary gas flow of 10 AU, sweep gas flow of 1 AU, and S lens RF level of 60 V. During the full-scan acquisition, which ranged from 58 to 870 m/z, the instrument operated at a 70,000 resolution (m/z=200), with an automatic gain control (AGC) target of $1\times10^6$ charges and a maximum injection time (IT) of 250 msec.

A systematic search for metabolites contained in a library of standard compounds (Mass Spectroscopy Metabolite Library of MSML® Standards, IROA Technologies™) was performed. In order to validate the identity of each detected metabolite, several criteria were required: a) the retention time of the metabolite detected must be within ±20 sec of the standard reference, b) the exact measured molecular exact mass of the metabolite must be within 10 ppm of the known mass of the reference compound, and c) the isotope ratios of the metabolite must match the standard reference.

The signal was calculated using Xcalibur® software (Thermo Fisher Scientific, San Jose, CA, USA) by integrating selected ion chromatographic peak area. The data output provides only metabolites for which standard compounds have been validated. The metabolites identified after positive and negative ESI mode analysis were combined to provide a non-redundant list of metabolites useful for statistical analysis. Metabolites with relative standard deviation (RSD) in QCs higher than that in samples were excluded. Only metabolites with RSD in QCs below 30% and identified in samples were kept for further analysis. Metabolites greater than 30% variance in QCs were not considered, except if significant variance was observed between groups, meaning that biological variability may exceed analytical variability.

Statistical Analysis

The statistical analysis was made by using the controller 20.

For microPET data, a voxel-based analysis was also used to assess the differences in cerebral FDG uptake between ultrasound neurostimulation mice and their control. The regions of interest were derived from Mirrione's templates using PMOD v3.2 software (PMOD Technologies Ltd, Switzerland) and applied to Z-score maps to obtain the Z-score values in these areas. Inter-group comparison was performed using a two-tail unpaired student t-test (XLSTAT). Differences were considered significant when $p<0.05$.

For metabolomic data, a first univariate statistical analysis by a Mann-Withney test (XLSTAT) was performed to select metabolites whose expression is significantly different between mice exposed to ultrasound neurostimulation and their control. Next, we also selected metabolites whose expression ratios between ultrasound neurostimulation and Sham were greater than 1.25 or less than 0.75. The pathway enrichment analysis was conducted by the free web software Metaboanalyst to map mouse metabolic pathways corresponding to metabolites selected prior to analysis. The pathway plots were based on the Kyoto Encyclopedia of Genes and Genomes (KEGG) database, and the National Center for Biotechnology Information (NCBI) database was searched to define gene functions. Only the metabolic pathways for which the FDR corrected statistics is significant were retained for discussion.

Acute Ultrasound Neurostimulation Induces Neural Activity in the Infralimbic Cortex Ultrasound waves were generated using a 500 kHz single-element transducer 22.

Eighty-three male BALB/cByJRj mice were obtained from Janvier Labs (Le Genest-Saint-Isle, France), aged 9 weeks (29±1.5 g) at the start of experiments. Mice were housed in standard condition (12:12 light-dark cycle) and all experiments were compliant with Directive 2010/63/EU guidelines on animal ethics.

Thirty mice were used for setting-up ultrasound stimulation parameters with motor cortex stimulation, while fifty-three underwent the unpredictable chronic mild stress procedure (for more details on the timeline, see SI Appendix, section VI, Experimental layout).

In the preliminary cohort of thirty mice, the transducer 22 was targeted to the primary motor cortex M1 to determine the ultrasound parameters that produce reliable neural activation. Electromyographic recordings of the induced motor responses revealed that a pulse of 160 ms at peak negative pressure of 400 kPa was the most efficient set of parameters.

A transducer 22 column was positioned over the right forepaw cortical representation on the primary motor cortex M1 (bregma −0.25 mm, midline+1.5 mm), that is, in the left hemisphere. Using a threshold-hunt algorithm, the stimulation was set for peak negative pressure ranging from 50 kPa to 500 kPa, in steps of 50 kPa. Each intensity step was assessed by ten trials (10-sec apart) and gave a motor success score, expressed in percentage.

Twenty mice were first threshold-hunted without electrodes to analyze for muscle contraction. Ten distinct mice then underwent the same procedure with EMG recordings to analyze motor evoked potentials (MEPs). Subdermal electrodes were positioned in the right brachioradialis muscle group (active) and between the third and fourth carpometacarpal joints. Signals were acquired, with a sample rate of 2 kHz (PowerLab, AdInstrument, Australia) and analyzed in post-treatment (Labchart 7, AdInstrument, Australia). A band pass digital filter, between 300 Hz and 1 kHz, was applied, then the absolute value was taken on 301 samples. A single-event MEP was considered valid (motor success) when above 50 µVpp and was monitored up to a 100 milliseconds (ms) bin for late polysynaptic waves. Averaged MEP intensities were then obtained for each individual regardless of motor success.

Results

When targeting the primary motor cortex (M1), the generation of contralateral muscular responses is a standard indicator of the threshold intensity that produces reliable neural activation. Ultrasound waves were generated using a single-element transducer 22 with a central frequency of 500 kHz, coupled to a water-filled collimated column (d=10 millimeters) and operated on a stereotaxic frame. The transducer 22 had a diameter of 38 mm and was geometrically focused at 65 millimeters (mm), driven with an electrical signal generated by an arbitrary waveform generator and amplified with a power amplifier. (The applied peak negative acoustic pressure was varied from 50 kPa to 500 kPa using a pulse length of 160 ms (80,000 cycles). Ultrasound stimulation was turned off during 10 s between every consecutive bursts to avoid blunting of the motor responses. In the preliminary cohort, thirty animals were used and ultrasound stimulation of M1's right forepaw representation generated muscular responses at all acoustic pressures except at the lowest acoustic pressure 50 kPa. Twenty mice were first assessed without subdermal electrodes; this procedure avoids impairments in motor responses caused by the mechanical constraint of electrodes and allows to reduce isoflurane concentrations down to 0.1%.

Each intensity step was tested with 12 ultrasound stimuli, which gave a percentage of motor success (that is 6 motor responses out of 12 trials was interpreted as 50% motor success).

Stimuli were also given 10 s apart, to avoid blunting of subsequent motor responses. To avoid facilitation of desensitization biases, mice were assessed through one of these two sequences:
1) starting at 50 kPa, increasing by steps of 50 kPa until reaching 500 kPa, or
2) starting at 500 kPa, decreasing by steps of 50 kPa down to 50 kPa.

Choosing one or the other sequence for an individual was semi-randomized and equally distributed upon the cohort. The data at each pressure step was then averaged for the all cohort, and these values were fitted into a sigmoid curve using a Boltzmann equation of the form:

$$f(I) = O_{max} + \frac{O_{max} - O_{min}}{1 + e^{(I-I_0)/dI}}$$

Wherein:
$O_{max}$ is the highest output (set at 12),
$O_{min}$ the barest (set at 0),
$I_0$ is the input halfmaximal value, and
$dI$ the slope.

Electrode-free video recordings on this subset of twenty mice anesthetized with 0.1% gaseous isoflurane: the intensity-response relationship followed a sigmoidal curve. Pressures at 400 kPa and 500 kPa reached the plateau of the curve and produced respectively 90%±2.7% and 98%±1.1% motor success rates. The motor threshold excitation, that is, the peak negative pressure that produces 50% motor success, was at 250 kPa experimentally, and found near the same value on the sigmoid curve (see FIG. 3).

In the second part of the procedure, electromyographic (EMG) recordings were carried out on ten distinct mice anesthetized at a 1% isoflurane, which was gaseous concentration used for the subsequent chronic ultrasound neurostimulation treatments. The subdermal electrodes were positioned as follows:
the active electrode was placed in the brachioradialis muscle group,
the reference electrode was placed between the third and fourth digit of the paw and
the system was grounded at the base of the tail.

In this experiment, the peak average intensity of motor evoked potentials (MEPs) was observed at 400 kPa with 42.4±12.1 µVpp, significantly higher than the failure value at 100 kPa (F (4, 47)=3.11, p=0.025, Tukey's p=0.03; see FIG. 4).

Down-scaled MEP intensities were observed for failure pressures (between 100 kPa and 200 kPa), but this blunt was also obtained for the highest setting tested (500 kPa), while it peaked for 400 kPa. The relatively deep anesthesia used in our MEP procedure (1% isoflurane) might have modified the quality of motor signals at higher intensities: the concentrations used in most studies for MEP analysis (<0.25%) were too low to fit those of our ultrasound neurostimulation paradigm (1%).

It is thus reckoned that intensity thresholds found at 1% isoflurane could be more readily transposed to the treatment condition. Concurrently, motor responses could be diminished by slow-moving cortical spreading depolarization, occurring for lastly tested pressures (500 kPa). These observations underlie the need to finely tune ultrasound parameters to produce stimulations that are consistent over time and success.

This stimulus setting was used for subsequent ultrasound neurostimulation experiments, and one session of ultrasound neurostimulation was then defined as 60 stimuli repeated at 0.1 Hz (10 min) under gaseous anesthesia (1% isoflurane). This repetition pattern was chosen to avoid a potential decrease of neuronal response at higher frequencies.

To target the infralimbic cortex, equivalent of the anterior cingulate cortex in rodents, the center of the collimator was positioned at bregma +2 mm on the stereotaxic frame.

The functional resolution of acute ultrasound neurostimulation was explored on a subset of eight mice: four mice that received one active session of ultrasound neurostimulation were compared to four mice that received one sham session (deactivation of the transducer 22).

The immunolabelling of reactive neurons (c-Fos) supports that acute ultrasound neurostimulation elicited significant neural activation in prefrontal regions, specifically the infralimbic cortex (see FIG. 5) and the secondary motor cortex M as can be seen in the following table 1:

TABLE 1 c-Fos activity evoked by acute ultrasound neurostimulation

| Area | | Diff. | t-test | P |
|---|---|---|---|---|
| OL | | 32 ± 23 | 1.4 | 0.21 |
| PrL | | 15 ± 17 | 0.87 | 0.42 |
| infralimbic cortex | | 46 ± 18 | 2.6 | 0.040 |
| Cg | | 18 ± 8.6 | 2.1 | 0.083 |
| M2 | | 22 ± 6.4 | 3.5 | 0.013 |
| M1 | | 6.6 ± 3.8 | 1.8 | 0.13 |
| Ad | | 3.7 ± 10 | 0.36 | 0.73 |
| AMY | BLA | 9.5 ± 11 | 0.9 | 0.40 |
| | CeA | −17 ± 11 | 1.6 | 0.16 |
| dHipp | DG | 59 ± 34 | 1.7 | 0.13 |
| | CA3 | 86 ± 18 | 4.9 | 0.0026 |
| | CA1 | 37 ± 14 | 2.5 | 0.044 |
| vHipp | DG | 49 ± 13 | 3.8 | 0.0087 |
| | CA3 | 40 ± 13 | 3 | 0.023 |
| | CA1 | 46 ± 22 | 2.1 | 0.080 |

In table 1, the differences between means, the student t-tests and the corresponding p-values are presented for each cerebral region compared between one-session ultrasound neurostimulation and one-session Sham mice. The meaning of the abbreviations can be found in the section list of the abbreviations.

It appears that other regions near the stimulation site, such as the olfactory areas, the prelimbic cortex, the anterior cingulate cortex or the primary motor cortex, were not significantly affected.

Furthermore, distant effects appeared in connected subcortical regions, such as subfields of the dorsal and the ventral parts of the hippocampus. This is notably illustrated by FIG. 6.

Ultrasound Neurostimulation Treatment Acts on Anxiety-Related Behaviors

Chronic ultrasound neurostimulation treatment was then applied in the main cohort (n=53), subjected to UCMS from day 0 to day 35 as illustrated on FIG. 7.

Treatment was applied from day 29 to day 33 ("ultrasound neurostimulation"), while the sham condition ("Sham") followed the same procedure under anesthesia (1% isoflurane) with the transducer 22 deactivated. From day 38 to day 43, mice were tested for depressive-like and anxiety-related behaviors in several paradigms. Ultrasound neurostimulation treatment was assessed against the effects of a current antidepressant drug (i.e., fluoxetine, "Flx"), administered chronically through drinking water from day 7 on and controlled (vehicle, "Veh" on FIG. 7).

At day 38, mice were examined for nest-building, a daily living measure affected by chronic stress. The corresponding results are represented on FIG. 8. The ability to build a nest within 5 hours was affected by treatment ($F_{(3, 53)}=7.85$, $p=0.00022$). Only chronic ultrasound neurostimulation increased the score (max. 5) when compared to sham-treated mice ($p=0.001$), whereas fluoxetine treatment had no effect.

At day 40, mice were tested for depressive-like behaviors in a reward-maze paradigm, built of three successive chambers with a palatable biscuit laid in the center of the furthest. The corresponding results can be found on FIG. 9.

Flx treatment decreased three-fold the latency to travel across the apparatus and reach the food reward ($F_{(3, 53)}=4.17$, $p=0.010$; Veh vs Flx, $p=0.042$), while ultrasound neurostimulation did not produce significant effects (Sham vs ultrasound neurostimulation, $p=0.221$). The consumption of the reward, measured in bites per minute, was not modified by ultrasound neurostimulation treatment, but only by chronic fluoxetine ($F_{(3, 53)}=2.95$, $p=0.042$; Veh vs Flx, $p=0.033$).

At day 43, mice were tested for anxiety-related behaviors in the openfield task as illustrated by FIG. 10. Chronic ultrasound neurostimulation treatment decreased significantly the latency to enter the center area ($F_{(3,53)}=3.72$, $p=0.017$; Sham vs ultrasound neurostimulation: $p=0.014$), while Flx did not. Furthermore, ultrasound neurostimulation treatment increased the number of center-crossings ($F_{(3, 53)}=7.58$, $p=0.00029$; Sham vs ultrasound neurostimulation: $p=0.002$). Despite a qualitative increase in crossings, Flx did not significantly affect this behavior ($p<0.10$).

Ultrasound Neurostimulation Treatment Acts on Cortical and Subcortical Brain Metabolism FDG metabolism measurements at day 36 were achieved as represented in the images of FIG. 11. The study of FIG. 11 reveals that chronic ultrasound neurostimulation (n=10) increased activity in frontal cortical regions including the prelimbic/M2 area, and also in the orbitofrontal regions (when compared to sham-treated mice (n=10).

In addition, ultrasound neurostimulation increases significantly the metabolic activity in distant subcortical areas such as the dorsal and ventral striata, the thalamus, the dorsal part of the hippocampus, the periaqueductal gray matter (PAG) and the raphe nuclei.

Other regions underneath the target (e.g., anterior olfactory regions and dorsal peduncular cortex), do not display modified metabolic activities, nor do laterally adjacent regions such as somatosensory cortices, or the direct antero-posterior neighborhood.

Despite significant changes in FDG uptake, no correlation was found with the expression of modified behaviors by ultrasound neurostimulation as shown by the following results given in tables 2 and 3.

Table 2 illustrates the statistical significances for inter-group comparisons in FDG uptake by providing Z-score and d-value for several regions.

TABLE 2

Statistical significances for inter-group comparisons in FDG uptake

|  | Z-score | d-value |
| --- | --- | --- |
| OFC | 4.29 ± 0.92 | 1.09 |
| PrL | 3.25 ± 0.50 | 1.09 |
| Mot | 3.15 ± 0.46 | 1.07 |
| Som | 3.78 ± 0.75 | 1.00 |
| DStr | 2.95 ± 0.69 | 0.97 |
| VStr | 2.43 ± 0.62 | 0.91 |
| Thal | 2.68 ± 0.68 | 0.97 |
| Dhipp | 2.45 ± 0.61 | 0.95 |
| PAG | 2.53 ± 0.11 | 0.97 |
| Raphe | 2.59 ± 0.65 | 0.97 |

Table 3 illustrates the statistical significances for Behaviors×FDG uptake (Spearman correlation) in several cases which are the nest-building, the reward maze (latency and consumption) and open-field (latency and center).

TABLE 3

Statistical significances for Behaviors × FDG uptake (Spearman correlation)

|  | Nest-building | Reward maze (latency) | Reward maze (consumption) | Open-field (latency) | Open-field (center) |
| --- | --- | --- | --- | --- | --- |
| OFC | 0.180 | 0.310 | 0.083 | 0.939 | 0.148 |
| PrL | 0.331 | 0.333 | 0.083 | 0.939 | 0.383 |
| Mot | 0.408 | 0.144 | 0.083 | 0.535 | 0.939 |
| Som | 0.145 | 0.159 | 0.083 | 0.645 | 0.253 |
| DStr | 0.180 | 0.310 | 0.083 | 6.939 | 0.148 |
| VStr | 0.053 | 0.333 | 0.252 | 0.645 | 0.094 |
| Thal | 0.579 | 0.558 | 0.211 | 0.645 | 0.294 |
| Dhipp | 0.307 | 1.000 | 0.393 | 0.535 | 0.702 |
| PAG | 0.141 | 0.139 | 0.080 | 0.585 | 0.310 |
| Raphe | 0.983 | 0.831 | 0.291 | 0.558 | 0.35 |

Ultrasound Neurostimulation Treatment Modifies the Metabolome in Cortical and Subcortical Areas Chronic ultrasound neurostimulation treatment (n=8) produced significant modifications in the metabolome of interconnected brain 14 regions involved in the UCMS model and major depression: the cingulate cortex, the prelimbic/infralimbic cortex (PrL/infralimbic cortex), the amygdala and the hippocampus.

In cortical areas, ultrasound neurostimulation had a relatively low impact on the metabolome of the anterior cingulate cortex since no metabolic pathway was found significantly disturbed, despite 9 metabolites showing significantly different concentrations compared to Sham mice as illustrated by table 4. In this table, the total number of metabolites showing FC<0.75 or FC >1.25 is given for both areas.

TABLE 4

Metabolites significantly modified by ultrasound neurostimulation in the Cg cortex

| Metabolites (n = 86) | FC | p-value |
| --- | --- | --- |
| Phenylacetic acid | 2.50 | 0.002 |
| Glucosamine 6-phosphate | 2.60 | 0.014 |
| Lipoamide | 1.95 | 0.029 |
| Pyridoxamine | 2.29 | 0.040 |
| Cysteine | 0.47 | 0.040 |
| Guanosine 5'-Monophosphate | 2.13 | 0.040 |
| Glutamine | 2.12 | 0.040 |

TABLE 4-continued

Metabolites significantly modified by ultrasound neurostimulation in the Cg cortex

| Metabolites (n = 86) | FC | p-value |
| --- | --- | --- |
| Homocystine | 0.77 | 0.040 |
| Creatine | 1.16 | 0.040 |

In ultrasound neurostimulation mice, the elevation of glutamine levels in the cingulate cortex was found positively correlated to the number of center crossings in the open-field task. This is notably shown by table 5 reproduced below wherein a Spearman correlation of p=0.036 can be observed.

TABLE 5

Statistical significances for Behaviors × Metabolites (Spearman correlation) in the Cingulate cortex

|  | Nest-building | Reward maze (latency) | Reward maze (consumption) | Open-field (latency) | Open-field (center) |
| --- | --- | --- | --- | --- | --- |
| Creatine | 0.736 | 0.403 | 0.445 | 0.432 | 0.645 |
| Glucosamine 6-phosphate | 0.900 | 0.788 | 0.393 | 0.939 | 0.702 |
| Guanosine 5'-Monophosphate | 0.704 | 0.478 | 0.805 | 0.180 | 0.702 |
| Homocystine | 0.641 | 0.531 | 0.140 | 0.119 | 0.148 |
| L-Cysteine | 0.053 | 0.144 | 0.252 | 0.760 | 0.215 |
| L-Glutamine | 0.382 | 0.452 | 0.501 | 0.052 | 0.036 |
| L-Phenylalanine | 0.408 | 0.058 | 0.252 | 0.294 | 0.879 |
| Lipoamide | 0.610 | 0.452 | 0.679 | 0.119 | 0.337 |
| Pyroxidamine | 0.408 | 0.728 | 0.174 | 0.760 | 1.000 |

In the PrL/infralimbic cortex of ultrasound neurostimulation mice, the study of tables 6 and 7 which follow shows that 6 metabolites were significantly modified compared to Sham mice, including the decrease of glutamic acid/glutamate concentrations.

TABLE 5

Metabolites significantly modified by ultrasound neurostimulation in the PrL/infralimbic cortex

| Metabolites (n = 83) | FC | p-value |
| --- | --- | --- |
| Trans-aconitate | 1.37 | 0.009 |
| 4-Hydroxy-D-proline | 2.88 | 0.020 |
| Homovanillate | 0.52 | 0.020 |
| Glutamic acid | 0.37 | 0.029 |
| Hypoxanthine | 2.79 | 0.040 |
| 1-NH2-Cyclopropane-1-Carboxylate | 1.48 | 0.040 |

TABLE 6

Statistical significances for Behaviors × Metabolites (Spearman correlation) in the Prelimbic/Infralimbic cortex

|  | Nest-building | Reward maze (latency) | Reward maze (consumption) | Open-field (latency) | Open-field (center) |
| --- | --- | --- | --- | --- | --- |
| 1-NH2-Cyclopropane-1-carboxylate | 0.240 | 0.102 | 0.083 | 0.432 | 0.760 |
| 4-Hydroxy-D-proline | 0.408 | 0.478 | 0.869 | 0.760 | 0.760 |
| Glutamic acid | 0.933 | 0.289 | 0.935 | 0.482 | 0.589 |

TABLE 6-continued

Statistical significances for Behaviors × Metabolites
(Spearman correlation) in the Prelimbic/Infralimbic cortex

| | Nest-building | Reward maze (latency) | Reward maze (consumption) | Open-field (latency) | Open-field (center) |
|---|---|---|---|---|---|
| Homovanillate | 0.933 | 0.788 | 0.343 | 0.879 | 0.482 |
| Hypoxanthine | 0.240 | 0.641 | 0.174 | 0.879 | 0.819 |
| Trans-aconitate | 0.900 | 0.728 | 0.869 | 0.760 | 0.760 |

As can be derived from table 7 reproduced below, five metabolic pathways were found disrupted, including arginine-proline metabolism (false discovery rate (FDR)=7.8× 10−4), alanine metabolism, aspartate and glutamate (FDR=0.016), glutathione metabolism (FDR=0.017), histidine metabolism (FDR=0.024), glycine metabolism, serine and threonine (FDR=0.035) and aminoacyl-tRNA biosynthesis (FDR-0.038; Table II).

TABLE 7

Metabolic pathways significantly modified by ultrasound neurostimulation in the Cg and the PrL/infralimbic cortex

| Pathway | FDR |
|---|---|
| Alanine, aspartate and glutamate metabolism | 0.0426 |
| Aminoacyl-tRNA biosynthesis Prelimbic/Infralimbic cortex | 0.0426 |
| Arginine and proline metabolism | 0.0007 |
| Alanine, aspartate and glutamate metabolism | 0.0164 |
| Glutathione metabolism | 0.0174 |
| Glycine, serine and threonine metabolism | 0.0352 |
| Aminoacyl-tRNA biosynthesis | 0.038 |
| Histidine metabolism | 0.024 |

Tables 8 to 10 show results obtained for the amygdala. More precisely, table 8 shows the total number of metabolites showing FC<0.75 or FC >1.25 in this area, table 9 deals with the Spearman correlations and table 10 proposes the metabolic pathways significantly modified by the ultrasound neurostimulation.

TABLE 8

Metabolites which are significantly modified by
ultrasound neurostimulation in the Amygdala

| Metabolites (n = 60) | FC | p-value |
|---|---|---|
| Malate | 0.45 | 0.001 |
| Glutamine | 2.32 | 0.014 |
| Uridine | 0.76 | 0.014 |
| N-Acetylneuraminate | 0.67 | 0.020 |
| beta-Alanine | 0.71 | 0.029 |
| Alanine | 0.71 | 0.029 |
| Adipic acid | 0.66 | 0.040 |

TABLE 9

Statistical significances for Behaviors ×
Metabolites (Spearman correlation) in the Amygdala

| | Nest-building | Reward maze (latency) | Reward maze (consumption) | Open-field (latency) | Open-field (center) |
|---|---|---|---|---|---|
| Adipic acid | 0.044 | 0.403 | 0.741 | 0.879 | 0.253 |
| beta-Alanine | 0.579 | 0.355 | 0.679 | 0.148 | 0.702 |
| L-Alanine | 0.579 | 0.355 | 0.679 | 0.148 | 0.702 |
| L-Glutamine | 0.307 | 0.021 | 0.252 | 0.180 | 0.760 |
| Malate | 0.900 | 0.699 | 0.393 | 0.879 | 0.760 |
| NAcetylneuraminate | 0.491 | 0.016 | 0.679 | 0.071 | 0.589 |
| Uridine | 0.736 | 0.058 | 0.935 | 0.052 | 0.094 |

TABLE 10

Metabolic pathways significantly modified by
ultrasound neurostimulation in the amygdala

| Pathway | FDR |
|---|---|
| Aminoacyl-tRNA biosynthesis | $4.48 \times 10^{-5}$ |
| Arginine and proline metabolism | 0.000183 |
| Nitrogen metabolism | 0.00246 |
| beta-Alanine metabolism | 0.00246 |
| Alanine, aspartate and glutamate metabolism | 0.0114 |
| Histidine metabolism | 0.0121 |
| Glutathione metabolism | 0.0121 |
| Glycine, serine and threonine metabolism | 0.024 |
| Ubiquinone and other terpenoid-quinone biosynthesis | 0.0264 |
| Lysine biosynthesis | 0.0466 |

Studying the tables 8 to 10 enables to show that, in the amygdala, 7 metabolites were found significantly modified. Nine metabolic pathways were also found significantly disturbed including aminoacyltRNA biosynthesis (FDR=$4.48 \times 10^{-5}$), abnormalities in lysine biosynthesis (FDR=0.046), in addition alanine, aspartate and glutamate metabolism (FDR=0.011).

Tables 11 to 13 show results obtained for the hippocampus. More precisely, table 11 shows the total number of metabolites showing FC<0.75 or FC >1.25 in this area, table 12 deals with the Spearman correlations and table 13 proposes the metabolic pathways significantly modified by the ultrasound neurostimulation.

TABLE 11

Metabolites which are significantly modified by
ultrasound neurostimulation in the hippocampus

| Metabolites (n = 72) | FC | p-value |
|---|---|---|
| Phenylalanine | 0.42 | 0.014 |
| Ornithine | 1.33 | 0.014 |
| Homoserine | 2.89 | 0.029 |
| Urocanate | 0.42 | 0.040 |
| Valine | 2.01 | 0.040 |

TABLE 12

Statistical significances for Behaviors x
Metabolites (Spearman correlation) in the hippocampus

|  | Nest-building | Reward maze (latency) | Reward maze (consumption) | Open-field (latency) | Open-field (center) |
|---|---|---|---|---|---|
| Homoserine | 0.028 | 0.041 | 0.805 | 0.294 | 0.589 |
| L-Ornithine | 0.491 | 0.848 | 0.174 | 0.760 | 0.589 |
| L-Phenylalanine | 0.261 | 0.102 | 0.741 | 0.119 | 0.879 |
| L-Valine | 0.307 | 0.268 | 0.935 | 0.294 | 0.535 |
| Urocanate | 0.610 | 0.558 | 0.679 | 0.119 | 0.589 |

TABLE 13

Metabolic pathways significantly modified by ultrasound
neurostimulation in the hippocampus

| Pathway | FDR |
|---|---|
| Aminoacyl-tRNA biosynthesis | $2.16 \times 10^{-7}$ |
| Alanine, aspartate and glutamate metabolism | 0.00416 |
| Nitrogen metabolism | 0.00416 |
| Arginine and proline metabolism | 0.0128 |
| Glutathione metabolism | 0.0229 |

Studying the tables 11 to 13 enables to show that ultrasound neurostimulation also shows a significant impact on the hippocampus, with 5 metabolites being significantly modified. Five metabolic pathways were also significantly modified including aminoacyl-tRNA biosynthesis (FDR=$2.16 \times 10^{-7}$), alanine-aspartate-glutamate and nitrogen metabolisms (FDR=0.004), arginine-proline metabolisms (FDR=0.013), and glutathione metabolism (FDR=0.023).

Despite long-term changes in the metabolome of the hippocampus, no effects of ultrasound neurostimulation were seen on the proliferation of newborn neurons in the dentate gyrus, a key mechanism to the function of classic antidepressants.

Indeed, on the last day of the experiments, ultrasound neurostimulation and Sham mice (n=4/group) were injected with an overdose of pentobarbital (Dolethal®) and the brains 14 were harvested and treated as described will now be described to achieve a c-Fos analysis Ninety minutes after a unique session of ultrasound neurostimulation or sham condition, mice were injected (i.p.) with an overdose of pentobarbital (Dolethal®), transcardially perfused with 40 mL of saline (0.9% NaCl) to remove the blood reservoir, then perfused with 100 ml of 4% paraformaldehyde (PFA). The brains 14 were harvested, left in 4% PFA overnight then put into a sucrose solution (20%) at 4° Celsius for 48 hours. The brains 14 were then snap-frozen in dry-ice-cooled isopentane and stored at −80° Celsius before the rest of the procedure. To be processed for immunohistochemistry (IHC), the brains 14 were cut into 40-µm coronal sections with a cooled microtome (−20° Celsius, Leica CM 3050 S). A classical method was employed for free-floating IHC. After endogenous peroxydase blockade (20 min, 50% EtOH, 1% H2O2), sections were processed with primary antibodies directed against c-Fos (1:1000, SC-52-G goat polyclonal IgG, Santa Cruz Biotechnologies) in phosphate buffer (PB) 0.1 M, 2% Normal Donkey Serum and 0.1% Triton for 48 hours at 4° C. Then a secondary incubation (1:500, Biotin-SP-conjugated AffiniPure donkey anti-goat IgG, Jackson ImmunoResearch) was performed 2 hours at room temperature. Finally, a standard protocol was used with 1-hour 1%-avidin/1%-biotin complex (Vectastain Elite ABC kit) and 3,3'-di-amino-benzidine revelation (SIGMAFAST™ DAB tablets, Sigma-Aldrich) for 3 minutes.

The immunolabelled sections were observed under a Zeiss Z.2 Imager microscope in transmitted light mode. Micrographs (magnificence ×10) were exported to the processor ImageJ in grayscale 8-bit format and converted to a fixed binary mask at 60% of background's mean gray value, which produced a count of c-Fos-positive (c-Fos+) cells in a selected region of interest. To analyze c-Fos activity patterns associated to one session of ultrasound neurostimulation or anesthesia, ubiquitous sections were picked for the olfactory areas, the prelimbic cortex, the infralimbic cortex, the anterior cingulate cortex, the primary motor cortex and the secondary motor cortex by an investigator blinded to the identity of each individual. Furthermore, subcortical regions connected to prefrontal regions were evaluated: 1) the amygdala and its subfields: the basolateral amygdala and central amygdala, and 2) the dorsal/ventral hippocampus and its subfields: the dentate gyrus, the CA3 and the CA1. The number of c-Fos+ cells in each region of interest was expressed as normalized cellular densities (c-Fos+ cells/$mm^2$).

In other words, to evaluate the effects of the ultrasound neurostimulation treatment on neurogenesis, fluorescence IHC was performed on 40-µm thick coronal sections. The doublecortin protein (DCX) was labelled to observe newborn neurons, while the Ki67 protein was labelled to observe proliferating cells. Double-stained cells were also taken into account. A classic method was employed, with a primary incubation (1:500 goat anti-DCX, 1:500 rabbit anti-Ki67) at 4° Celsius for 24 hours and a secondary incubation (1:400 donkey anti-goat 555 nm DsRed, 1:400 donkey anti-rabbit 488 nm GFP) at room temperature for 2 hours. Both incubations were done in PB 0.1 M, 2% Normal Donkey Serum and 0.1% Triton and followed by a 15-min washing period in PB 0.1 M (3×5 min). The sections were mounted with DAPI (VECTASHIELD Hard Set with DAPI) to label the nucleus of each cell, then observed under a Zeiss Z.2 Imager microscope. For each individual, DCX+, Ki67+ and DCX+/Ki67+ cells were counted in the granular layer of the dentate gyrus in 8 ubiquitous sections along the antero-posterior axis of the brain 14. Cells counts were expressed as cellular densities (/$mm^2$).

The analysis revealed no difference between ultrasound neurostimulation and Sham mice as shown in FIG. 12 which illustrates newborn neurons and proliferating cells in the dendrite gyrus of the hippocampus following chronic ultrasound neurostimulation treatment.

Despite an immediate effect of one session of ultrasound neurostimulation on c-Fos densities in the hippocampus and the modification of metabolic pathways following the chronic application of ultrasound neurostimulation, proliferation mechanisms in the dentate gyrus were not readily engaged in the present case. Because neurogenesis has been associated to antidepressant effects, the fact that ultrasound neurostimulation does not promote the proliferation of newborn neurons could be associated to the lack of effects on depressive-like behaviors, measured in the reward-maze test.

DISCUSSION

Numerous brain 14 structures are paramount to the pathophysiology of major depression, but the growing need to act therapeutically on these regions is only partially answered by current neurostimulation techniques. This study used ultrasound waves to non-invasively target the infralimbic cortex (subgeneal anterior cingulate cortex equivalent) in a mouse model of major depression.

Chronic ultrasound neurostimulation treatment impacted various behavioral endpoints induced by the UCMS regimen as well as brain 14 metabolic activity on the site of stimulation (prefrontal cortex and its close surroundings) but also at distant, connected limbic areas, such as the striatum, the dorsal hippocampus and the raphe nucleus.

Measures of wellbeing (nest-building) and anxiety-related behaviors (open-field task) were enhanced by the ultrasound neurostimulation while items relative to anhedonia and reward-seeking were not affected compared to classic selective serotonin reuptake inhibitor treatment (i.e., fluoxetine).

Metabolites were modified at the target site and in the hippocampus, involving glutamate pathways that might correlate to longer-term changes in brain 14 plasticity.

The ability of ultrasound waves to reliably stimulate cortical regions through the cranium has been reproduced in the current study.

When applied during one session, ultrasound neurostimulation was able to evoke neural activity in the infralimbic cortex of mice with little spatial inaccuracy at stimulation site (collateral effects on M2).

On the one hand, surrounding brain 14 regions such as the PrL or the Cg were not readily affected by the ultrasound neurostimulation. Though, the distant hippocampal regions were affected by the acute application of ultrasound neurostimulation.

These results suggest that, similarly to standard M1 stimulation, a threshold pressure appears for patterns of repeated stimuli, under which the activation of a brain 14 region was not seen on immediate c-Fos labelling. Otherwise and given the geometric properties of the ultrasound beam, the lack of c-Fos activation in the PrL suggests that the spatial resolution of ultrasound neurostimulation is not directly correlated to its functional resolution.

Also, a narrower range of effective pressures could be responsible for the specific stimulation of the infralimbic cortex (1-mm wide between 350 kPa and 400 kPa) compared to motor cortex stimulation.

Also, the auditory cortex was not affected by ultrasound neurostimulation, which further supports a functional targeting of the infralimbic cortex.

Since c-Fos labelling does not discriminate between glutamatergic and GABAergic neurons, the results show that brain 14 regions might react differently to ultrasound neurostimulation. As ultrasound neurostimulation is described to preferentially act on axons rather than somas, the reactivity of a brain 14 region to its application might depend on the orientation of the stimulation, as it has been shown for transcranial magnetic stimulation.

When applied chronically for 5 days, some behavioral measures were modified by ultrasound neurostimulation. As an indicator of well-being in rodents, the onset of nest-building was reduced by ultrasound neurostimulation, while it was not affected by fluoxetine (similar effects of the drugs were previously reported). Because such daily living activities can be negatively regulated by chronic stress and major depression, ultrasound neurostimulation showed beneficial effects on this aspect of the UCMS model.

Furthermore, ultrasound neurostimulation treatment seemed to reduce anxiety-like behaviors: measures of latency and center-crossings were found significantly different from sham-treated mice in the open-field task.

On the other hand, the anhedonic measure of reward consumption was not ameliorated and did not match the results of fluoxetine treated mice.

It was reported that a single session of isoflurane anesthesia could induce antidepressant-like effects and increase glutamatergic transmission in the hippocampus, however, the sham-treated group displayed baseline behaviors statistically equal to vehicle-treated mice, suggesting that our present results are specific to the ultrasound neurostimulation treatment.

Chronic ultrasound neurostimulation modified brain 14 metabolic activity 72 hours after the last treatment session.

The uptake of FDG was increased near the target site at bregma +2 mm in prefrontal regions (mostly the PrL and OFC) and in M2. Because this latter region cannot be presently linked to brain 14 modifications induced by the UCMS regimen and more broadly in major depression, the increased activity might be a direct effect of the ultrasound neurostimulation retaining some spatial biases as shown for acute ultrasound neurostimulation.

Other regions within a 1.5-mm radius of the stimulation site did not appear modified during microPET imaging, suggesting that only the most intense portion of the ultrasound beam acts upon the target also in this timespan.

The brain 14 metabolic activity was also increased in distant areas (striatum, thalamus, dorsal hippocampus, raphe nucleus and PAG), which could mean that ultrasound neurostimulation acted at distance from the prefrontal target through functional connectivity, which is supported by the effects of acute ultrasound neurostimulation on the hippocampus.

The effective stimulation of such projections might take part in the behavioral effects of ultrasound neurostimulation: hippocampal-prefrontal communication is considered crucial in the pathophysiology of major depression, and the connectivity of the PrL/infralimbic cortex to the raphe nucleus has been identified in rats to play a role in behavioral control of stressors, which could be related to the decrease of anxiety-related behaviors.

Furthermore, it was shown that major depression was associated in PET-Scan imaging with an hypoactivation of frontal regions and that therapeutic response to fluoxetine could revert that type of metabolic changes by increasing cortical activity failure to respond to classic selective serotonin reuptake inhibitor treatment was associated with an absence of cortical modification.

The effects of ultrasound neurostimulation on cortical metabolism, and more specifically the prefrontal regions, could have participated to the modification of the UCMS-induced phenotype. Although the correlation study did not show significance between FDG uptake and behaviors in this timespan, cortical changes could be at play in the top-down regulation of anxiety-related behaviors, but would require larger sample size to argue.

Ten days after the last treatment session, cortical (Cg, PrL/infralimbic cortex) and subcortical structures (amygdala and hippocampus) displayed significant changes in metabolic pathways following ultrasound neurostimulation.

The correlation study showed that glutamine levels in the Cg was positively correlated with the number of center crossings in the open-field suggesting that long-term changes in the metabolome might act on the modification of anxiety-related behaviors observed in ultrasound neurostimulated mice.

Furthermore, glutamate pathways were similarly modified in all studied regions and more specifically, decreased levels of glutamate were observed in the PrL/infralimbic cortex. Previous studies reported increased glutamate levels in the serum and in frontal areas of major depression patients. In rodents, glutamate is implicated in the expression of depressive-like and anxiety-related behaviors.

Furthermore, glutamate pathways in the hippocampus, but not the prefrontal cortex, might be pivotal to antidepressant response in selective serotonin reuptake inhibitors-treated mice. The current findings thus show that the effects of ultrasound neurostimulation on glutamine and glutamate pathways could be associated to a therapeutic response similarly to classic fluoxetine treatment, although both treatments did not modify the same behaviors in the UCMS model.

Also, other hippocampal functions, such as neurogenesis, were not modified by ultrasound neurostimulation, which further supports that the behavioral effects were mainly observed on anxiety and not directly on anhedonic features.

Also, few metabolic modifications were seen in the Cg even though this structure was in the propagation path of the ultrasound beam.

Direct interneuron regulation between the structures could have been at play and thus participated in reversing prefrontal abnormalities induced by UCMS. Glutamate variations in other brain 14 regions such as the PAG have also been linked to depressive-like behavior and chronic stress. Analysis of this region was beyond the scope of our study, although FDG metabolism was modified by chronic ultrasound neurostimulation treatment.

CONCLUSION

In this experimental section, the potential of ultrasound neurostimulation in an unpredictable chronic mild stress model was evaluated. In comparison to pharmacological treatment (fluoxetine), our results showed that selected ultrasound application on the prefrontal cortex counteracts some behavioral modifications induced by the UCMS regimen and decreases anxiety-related behaviors. Besides, chronic ultrasound neurostimulation activated various brain 14 regions including areas at distance from the targeted zone as confirmed by microPET imaging and metabolomic analyses. The positive effects on anxiety-related behaviors supports the potential of ultrasound neurostimulation as a putative therapeutic tool for specific aspects of major depression.

General Conclusion

In this specification, it has been shown that focused ultrasound stimulation set by the neurostimulation device 10 ameliorates behaviors and modify distributed brain metabolism in a mouse model of chronic stress.

Such ultrasound stimulation is such that at least one parameter of the neurostimulation device 10 is tuned based on the provided motor threshold excitation, the tuning comprising setting the ultrasound power of the pulses so that the ratio between the ultrasound power of the pulses and the motor threshold excitation be superior or equal to 1.2.

Major depression is a severe mental illness and one of the most prevalent causes of disability worldwide. Current antidepressants (such as monoamine reuptake inhibitors) cannot achieve remission in all patients, a therapeutic dead-end referred as treatment-resistance. Known alternatives are neurostimulation techniques including transcranial magnetic fields and implantable electrodes, able to target and modulate some brain correlates of the disease. However, these techniques suffer major drawbacks such as poor spatial resolution and invasiveness.

Ultrasound (US) waves have recently been used in such paradigms to act upon the motor cortex or the hippocampus through the skull of rodents. This novel technique could circumvent the limitations of magnetic fields and implanted electrodes by producing precise beams that can target non-invasively cortical or deeper structures. In this study, we evaluated the efficacy of US neurostimulation (USNS) in a mouse model of depression: the unpredictable chronic mild stress (UCMS).

Ultrasound waves were targeted to the infralimbic cortex (IL), the rodent's analog of the subgenual part of the anterior cingulate cortex (sgACC), a region implicated in the pathophysiology of depression. The therapeutic impact of USNS was assessed on depression-like and anxiety-related behaviors in treated and placebo animals and evaluated against the effects of a pharmacological drug (fluoxetine). Furthermore, USNS effects were analyzed at the brain level with microPET imaging and metabolomic studies of the targeted region and distant areas.

A single-element transducer (diameter: 38 mm, focused at 65 mm) coupled to a water-filled collimated column was operated in a full-fledge stereotaxic frame.

First, the ability of US stimulations to reliably produce neuronal activation was assessed on the primary motor cortex M1 of thirty mice, which generated motor responses upon stimulation. We were able to focus the subarea of M1 that controls contralateral forepaw movements. Under light anesthesia, the optimal parameters that were able to produce above 90% motor success was a US stimulation of 160 milliseconds (80,000 cycles) at 400 kPa peak negative pressure.

In the core experiment, during the fifth week of the UCMS regimen, mice received chronic stimulations over the IL. US application (160 msec, 400 kPa) was repeated 60 times at 0.1 Hz (total exposure time of 10 minutes) every 24 hours for five days. The effects of the USNS (n=15 mice) were assessed against anesthetized controls (n=15) and a classic pharmacological drug: fluoxetine (n=12).

Results: USNS was able to improve daily living measures, such as nest-building, and also reduced anxiety-related behaviors in the open-field task.

Three days after the last USNS session, brain metabolism was modified specifically on target site (prefrontal regions), but also in distant, connected areas relevant to depression (striatum, hippocampus, raphe nucleus). Further analysis carried out 10 days after the last session revealed that the IL, the amygdala and the hippocampus showed altered metabolic pathways. Glutamate metabolism, documented to be modified in depressed patients, was altered in the IL and the hippocampus, a region that plays a primary role in the therapeutic approach of depression.

Targeted USNS of the sgACC/IL was able to enhance behaviors in the mouse model of UCMS, acting on distributed brain networks. Brain metabolism was modified 3 days after treatment in the prefrontal cortex and distant areas, such as the hippocampus. Metabolism in these regions was modified 10 days post-treatment, with several altered pathways including glutamate. This study supports the growing interest of ultrasound as a novel neurostimulation strategy in the treatment of mental disorders.

LIST OF ABBREVIATIONS

ACC: anterior cingulate cortex
Ad: auditory cortex
ADs: antidepressants
AGC: automatic gain control AMY: amygdala
ASIC: application specific integrated circuit
AU: arbitrary unit(s)
BALB/c: albino, laboratory-bred strain of the house mouse
BLA: basolateral amygdala
CD-ROM: compact disc read-only memory
CeA: central amygdala
Cg: anterior cingulate cortex
CMUT: capacitive micromachined ultrasound transducers
CPU: central processing unit
CT: computed tomography
DAPI: 4',6-diamidino-2-phenylindole
DBS: deep brain stimulation
DCX: doublecortin
DG: dentate gyrus
dlPFC: dorsolateral prefrontal cortex
DHIpp: dorsal hippocampus
DMStr: dorsomedial striatum
DSP: digital signal processor
DStr: dorsal striatum
DVD: digital versatile disk
EEG: electroencephalography
EEPROM: electrically erasable and programmable read only memory
EMG: electromyographic
EROM: erasable programmable read-only memory
ESI: electrospray ionization
FC: fold change
FDR: false discovery rate
FDG: fludeoxyglucose ($^{18}$F)
Flx: fluoxetine
FORTRAN: formula translator
FPGA: field programmable gate array
FWHM: full width at half maximum
GFP: green fluorescent protein
GPU: graphics processing unit
HESI: heated electrospray ionization
HTML: hypertext markup language
IHC: immunohistochemistry
IL: infralimbic cortex
IT: injection time
KEGG: Kyoto Encyclopedia of Genes and Genomes
LC-HRMS: liquid chromatography-high resolution mass spectrometry
MD: major depression
MDThal: mediodorsal thalamus
MEP: motor evoked potential
Mot: motor cortex
MRI: magnetic resonance imaging
M1: primary motor cortex
M2: secondary motor cortex
NS: non-stressed
OFC: orbitofrontal cortex
OL: olfactory areas (olfactory bulbs)
PAG: periacqueductal gray (matter)
PB: phosphate buffer
PC: personal computer
PCMCIA: personal computer memory card international association
PDA: personal digital assistant
PTSD: post-traumatic stress disorder
PET: positron-emission tomography
PET-Scan: positron-emission tomography scanner
PFA: paraformaldehyde
PLA: programmable logic arrays
PLD: programmable logic device
PrL: prelimbic cortex
QC: quality control
RAM: random access memory
RNA: Ribonucleic acid
ROM: read-only memory
ROI: region of interest
RSD: relative standard deviation
SD: standard deviation
SEM: mean standard error
SgACC: subgenual part of the anterior cingulate cortex
Sham: sham condition (condition of a subject that was administered placebo medicine in controlled environment)
Solv: solvent
Som: somatosensory cortex
SRAM: static random access memory
SSD: solid state drive disk
SSRI: selective serotonin reuptake inhibitors
Thal: thalamus
TRD: treatment resistant depression
UCMS: unpredictable chronic mild stress
US: ultrasound
USNS: ultrasound neurostimulation
Veh: vehicle
VHDL: VHSIC (very high speed integrated circuit) hardware description language
vHipp: ventral hippocampus
VMStr: ventromedial striatum
VStr: ventral striatum
WBM: whole brain mask

The invention claimed is:

1. Method for stimulating cerebral activity of a subject with a neurostimulation device, the method being computer-implemented and comprising the steps of:
providing a motor threshold excitation, the motor threshold excitation corresponding to the ultrasound power leading to 50% success of obtaining a motor response of the subject when stimulating the cerebral activity of the subject with the neurostimulation device, and is the value of a peak acoustic pressure in the subject when the ultrasound power is at a level wherein one excitation of the subject out of two excitations of the subject leads to a motor response of the subject, each of said excitations being a respective one of the ultrasound pulses, and
applying ultrasound pulses to the subject with the neurostimulation device with an ultrasound power of the neurostimulation device being based on the provided motor threshold excitation, in a manner wherein the ultrasound power of the ultrasound pulses fulfills a condition, the condition comprising a ratio between the ultrasound power of the ultrasound pulses and the motor threshold excitation being superior to or equal to 1.2.

2. A method according to claim 1, wherein the condition comprises the ratio between the ultrasound power of the ultrasound pulses and the motor threshold excitation being is inferior to or equal to 2.0.

3. A method according to claim 2, wherein the condition comprises the ratio between the ultrasound power of the pulses and the motor threshold excitation being between 1.4 and 1.8.

4. A method according to claim 3, wherein the condition comprises the ratio between the ultrasound power of the pulses and the motor threshold excitation being between 1.55 and 1.65.

5. A method according to claim 1, wherein the step of applying ultrasound pulses comprises applying the ultrasound pulses in the infralimbic cortex of the subject.

6. A method according to claim 1, wherein the step of applying ultrasound pulses comprises applying ultrasound pulses having a pulse repetition frequency, wherein the pulse repetition frequency fulfills a frequency condition, wherein the frequency condition is the pulse repetition frequency being between 400 kilohertz and 600 kilohertz.

7. A method according to claim 6, wherein the frequency condition comprises the pulse repetition frequency being between 450 kilohertz and 550 kilohertz.

8. A method according to claim 7, wherein the frequency condition comprises the pulse repetition frequency being between 490 kilohertz and 510 kilohertz.

9. A method according to claim 1, wherein the step of applying ultrasound pulses is configured as a step of applying an uninterrupted set of ultrasound pulses and as having a number of cycles, wherein the number of cycles is the number of the ultrasound pulses in the uninterrupted set of ultrasound pulses and wherein the number of cycles in the step fulfills a cycle number condition, wherein the cycle cumber condition comprises the number of cycles being between 75000 and 80000.

10. A method according to claim 1, wherein the step of applying ultrasound pulses comprises performing, in one day, a number of ultrasound applications, wherein each of the ultrasound applications comprises another set of uninterrupted ultrasound pulses, and wherein the number of ultrasound applications during the step of applying ultrasound pulses fulfills a number condition comprising performing, in one day between 40 and 60 of the ultrasound applications.

11. A method according to claim 10, wherein the number of applications condition comprises the number of ultrasound applications being between 45 and 55.

12. A method according to claim 11, wherein the number of applications condition comprises the number of ultrasound applications being between 48 and 52.

13. A method according to claim 1, wherein the subject is a mammal.

14. A method according to claim 13, wherein the mammal is a rodent.

15. A method according to claim 14, wherein the rodent is a mouse.

16. A method according to claim 1, wherein the step of applying ultrasound pulses is configured as a step of applying an uninterrupted set of ultrasound pulses and as having a number of cycles, wherein the number of cycles is the number of the ultrasound pulses in the uninterrupted set of ultrasound pulses, and wherein the number of cycles in the step fulfills a cycle number condition, wherein the cycle number condition comprises the number of cycles being between 78000 and 82000.

17. A method according to claim 16, wherein the cycle number condition comprises the number of cycles being between 79000 and 81000.

18. Method for modulating emotion of a subject or treating a neuropathological disorder of the subject or reducing anxiety like behavior of the subject, the method comprising the step of:
applying ultrasound pulses to the subject, wherein a power of the ultrasound pulses is based on a provided motor threshold excitation, wherein the power of the ultrasound pulses fulfills a condition, the condition comprising a ratio between the power of the ultrasound pulses and the motor threshold excitation being superior to or equal to 1.2,
wherein the motor threshold excitation is the value of a peak acoustic pressure in the subject when stimulating the cerebral activity of the subject with ultrasound pulses at an ultrasound power at which one excitation of the subject out of two excitations of the subject leads to a motor response of the subject, each of said excitations being a respective one of the ultrasound pulses.

19. A controller adapted to set parameters of a neurostimulation device before stimulating cerebral activity of a subject, the neurostimulation device comprising at least one ultrasound probe adapted to emit ultrasound pulses with a controllable ultrasound power, the neurostimulation device being adapted to stimulate cerebral activity by applying ultrasound pulses emitted by the at least one ultrasound probe, the controller being adapted to:
receive a motor threshold excitation, the motor threshold excitation corresponding to the ultrasound power leading to 50% success of obtaining a motor response of the subject when stimulating the cerebral activity of the subject with the neurostimulation device, and
perform a tuning of at least one parameter of the neurostimulation device based on the provided motor threshold excitation, wherein the tuning comprises setting the ultrasound power of the pulses so that the ratio between the ultrasound power of the pulses and the motor threshold excitation is superior to or equal to 1.2.

20. Neurostimulation device comprising:
one or more ultrasound probes, wherein the one or more ultrasound probes are adapted to emit ultrasound pulses with a controllable ultrasound power, and
a controller according to claim 19, connected to the one or more ultrasound probes,
the neurostimulation device being adapted to stimulate cerebral activity by applying ultrasound pulses emitted by the one or more ultrasound probes.

* * * * *